(12) United States Patent
Tong et al.

(10) Patent No.: US 8,491,606 B2
(45) Date of Patent: *Jul. 23, 2013

(54) MEDIAN LOBE RETRACTION APPARATUS AND METHOD

(75) Inventors: Ling-Kang Tong, Fremont, CA (US); Theodore C. Lamson, Pleasanton, CA (US); Joseph Catanese, III, San Leandro, CA (US); R. James Yu, Mountain View, CA (US); Daniel Merrick, Dublin, CA (US); Matthew McLean, San Francisco, CA (US); James W. Niederjohn, San Jose, CA (US); Floria Cheng, San Francisco, CA (US); Ben Thompson, San Carlos, CA (US); Brian Y. Tachibana, Oakland, CA (US); Kristin Taylor, San Ramon, CA (US); Earl A. Bright, II, Los Altos, CA (US)

(73) Assignee: Neotract, Inc., Pleasanton, CA (US)

( * ) Notice: Subject to any disclaimer, the term of this patent is extended or adjusted under 35 U.S.C. 154(b) by 117 days.

This patent is subject to a terminal disclaimer.

(21) Appl. No.: 12/979,065

(22) Filed: Dec. 27, 2010

(65) Prior Publication Data

US 2011/0144423 A1    Jun. 16, 2011

Related U.S. Application Data

(63) Continuation-in-part of application No. 12/852,243, filed on Aug. 6, 2010, now Pat. No. 8,333,776, and a continuation-in-part of application No. 12/512,674, filed on Jul. 30, 2009, now Pat. No. 8,216,254, and a continuation-in-part of application No. 11/775,162, filed on Jul. 9, 2007, and a continuation-in-part of application No. 11/671,914, filed on Feb. 6, 2007, now Pat. No. 8,157,815, and a continuation-in-part of application No. 11/492,690, filed on Jul. 24, 2006, now Pat. No. 7,896,891, and a continuation-in-part of application No. 11/833,660, filed on Aug. 3, 2007, and a continuation of application No. 11/318,246, filed on Dec. 22, 2005, now Pat. No. 7,645,286, and a continuation-in-part of application No. 11/838,036, filed on Aug. 13, 2007, now Pat. No. 7,914,542, which is a continuation of application No. 11/134,870, filed on May 20, 2007, now Pat. No. 7,758,594.

(60) Provisional application No. 61/084,937, filed on Jul. 30, 2008.

(51) Int. Cl.
*A61B 17/10* (2006.01)

(52) U.S. Cl.
USPC .......................................................... 606/139

(58) Field of Classification Search
USPC ................. 606/139, 153, 144–146, 148–151, 606/157, 232
See application file for complete search history.

(56) References Cited

U.S. PATENT DOCUMENTS

| 659,422 A | 10/1900 | Shidler |
| 780,392 A | 1/1905 | Wanamaker et al. |

(Continued)

FOREIGN PATENT DOCUMENTS

| DE | 10159470 | 6/2003 |
| EP | 0246836 | 12/1991 |

(Continued)

OTHER PUBLICATIONS

Richard Berges et al., "Alternative Minimalinvasive Therapien Beim Benignen Prostatasyndrom", Medizin, Jg. 104, Heft 37, Sep. 14, 2007.

(Continued)

*Primary Examiner* — Gregory Anderson
(74) *Attorney, Agent, or Firm* — Steptoe & Johnson LLP

(57) ABSTRACT

A system and associated method for manipulating tissues and anatomical or other structures in medical applications for the purpose of treating diseases or disorders or other purposes. In one aspect, the system includes a delivery device configured to deploy and implant anchor devices for comprising, distracting and/or retracting the lobes of a prostate.

24 Claims, 21 Drawing Sheets

U.S. PATENT DOCUMENTS

| | | | |
|---|---|---|---|
| 789,467 A | 5/1905 | West | |
| 2,579,192 A | 12/1951 | Kohl | |
| 2,646,298 A | 7/1953 | Leary | |
| 2,697,624 A | 12/1954 | Thomas et al. | |
| 2,734,299 A | 2/1956 | Masson | |
| 2,825,592 A | 3/1958 | Semple | |
| 3,326,586 A | 6/1967 | Frost et al. | |
| 3,470,834 A | 10/1969 | Bone | |
| 3,521,918 A | 7/1970 | Hammond | |
| 3,664,345 A | 5/1972 | Dabbs et al. | |
| 3,713,680 A | 1/1973 | Pagano | |
| 3,716,058 A | 2/1973 | Tanner, Jr. | |
| 3,756,638 A | 9/1973 | Stockberger | |
| 3,873,140 A | 3/1975 | Bloch | |
| 3,875,648 A | 4/1975 | Bone | |
| 3,931,667 A | 1/1976 | Merser et al. | |
| 3,976,079 A | 8/1976 | Samuels et al. | |
| 4,006,747 A | 2/1977 | Kronenthal et al. | |
| 4,210,148 A | 7/1980 | Stivala | |
| 4,235,238 A | 11/1980 | Ogiu et al. | |
| 4,291,698 A | 9/1981 | Fuchs et al. | |
| 4,409,974 A | 10/1983 | Freedland | |
| 4,493,323 A | 1/1985 | Albright et al. | |
| 4,513,746 A | 4/1985 | Aranyi | |
| 4,621,640 A | 11/1986 | Mulhollan et al. | |
| 4,657,461 A | 4/1987 | Smith | |
| 4,669,473 A | 6/1987 | Richards et al. | |
| 4,705,040 A | 11/1987 | Mueller et al. | |
| 4,714,281 A | 12/1987 | Peck | |
| 4,738,255 A | 4/1988 | Goble et al. | |
| 4,741,330 A | 5/1988 | Hayhurst | |
| 4,744,364 A | 5/1988 | Kensey | |
| 4,750,492 A | 6/1988 | Jacobs | |
| 4,762,128 A | 8/1988 | Rosenbluth | |
| 4,823,794 A | 4/1989 | Pierce | |
| 4,863,439 A * | 9/1989 | Sanderson | 604/264 |
| 4,899,743 A | 2/1990 | Nicholson et al. | |
| 4,926,860 A | 5/1990 | Stice et al. | |
| 4,946,468 A | 8/1990 | Li | |
| 4,955,913 A | 9/1990 | Robinson | |
| 4,968,315 A | 11/1990 | Gatturna | |
| 5,002,550 A | 3/1991 | Li | |
| 5,041,129 A | 8/1991 | Hayhurst et al. | |
| 5,046,513 A | 9/1991 | Gatturna et al. | |
| 5,053,046 A | 10/1991 | Janese | |
| 5,080,660 A | 1/1992 | Buelna | |
| 5,100,421 A | 3/1992 | Christoudias | |
| 5,123,914 A | 6/1992 | Cope | |
| 5,129,912 A | 7/1992 | Noda et al. | |
| 5,192,303 A | 3/1993 | Gatturna et al. | |
| 5,203,787 A | 4/1993 | Noblitt et al. | |
| 5,207,672 A | 5/1993 | Roth et al. | |
| 5,217,470 A | 6/1993 | Weston | |
| 5,217,486 A | 6/1993 | Rice et al. | |
| 5,234,454 A | 8/1993 | Bangs | |
| 5,236,445 A | 8/1993 | Hayhurst et al. | |
| 5,258,015 A | 11/1993 | Li et al. | |
| 5,267,960 A | 12/1993 | Hayman et al. | |
| 5,269,802 A | 12/1993 | Garber | |
| 5,269,809 A | 12/1993 | Hayhurst et al. | |
| 5,322,501 A | 6/1994 | Mahmud-Durrani | |
| 5,330,488 A | 7/1994 | Goldrath | |
| 5,334,200 A | 8/1994 | Johnson | |
| 5,336,240 A | 8/1994 | Metzler et al. | |
| 5,354,271 A | 10/1994 | Voda | |
| 5,358,511 A | 10/1994 | Gatturna et al. | |
| 5,364,408 A | 11/1994 | Gordon | |
| 5,366,490 A | 11/1994 | Edwards et al. | |
| 5,368,599 A | 11/1994 | Hirsch et al. | |
| 5,370,646 A | 12/1994 | Reese et al. | |
| 5,380,334 A | 1/1995 | Torrie et al. | |
| 5,391,182 A | 2/1995 | Chin | |
| 5,403,348 A | 4/1995 | Bonutti | |
| 5,405,352 A | 4/1995 | Weston | |
| 5,411,520 A | 5/1995 | Nash et al. | |
| 5,417,691 A | 5/1995 | Hayhurst | |
| 5,435,805 A | 7/1995 | Edwards et al. | |
| 5,470,337 A | 11/1995 | Moss | |
| 5,472,446 A | 12/1995 | de la Torre | |
| 5,480,406 A | 1/1996 | Nolan et al. | |
| 5,499,994 A | 3/1996 | Tihon et al. | |
| 5,501,690 A | 3/1996 | Measamer et al. | |
| 5,507,754 A | 4/1996 | Green et al. | |
| 5,522,846 A | 6/1996 | Bonutti | |
| 5,531,763 A | 7/1996 | Mastri et al. | |
| 5,536,240 A | 7/1996 | Edwards et al. | |
| 5,540,704 A | 7/1996 | Gordon et al. | |
| 5,545,171 A | 8/1996 | Sharkey et al. | |
| 5,545,178 A | 8/1996 | Kensey et al. | |
| 5,550,172 A | 8/1996 | Regula et al. | |
| 5,554,162 A | 9/1996 | DeLange | |
| 5,554,171 A | 9/1996 | Gatturna et al. | |
| 5,562,689 A | 10/1996 | Green et al. | |
| 5,569,305 A | 10/1996 | Bonutti | |
| 5,571,104 A | 11/1996 | Li | |
| 5,573,540 A | 11/1996 | Yoon | |
| 5,578,044 A | 11/1996 | Gordon et al. | |
| 5,591,177 A | 1/1997 | Lehrer | |
| 5,593,421 A | 1/1997 | Bauer | |
| 5,611,515 A | 3/1997 | Benderev et al. | |
| 5,626,614 A | 5/1997 | Hart | |
| 5,630,824 A | 5/1997 | Hart | |
| 5,647,836 A | 7/1997 | Blake, III et al. | |
| 5,665,109 A | 9/1997 | Yoon | |
| 5,667,486 A | 9/1997 | Mikulich et al. | |
| 5,669,917 A | 9/1997 | Sauer et al. | |
| 5,690,677 A | 11/1997 | Schmiedling et al. | |
| 5,697,950 A | 12/1997 | Fucci et al. | |
| 5,707,394 A | 1/1998 | Miller et al. | |
| 5,716,368 A | 2/1998 | de la Torre et al. | |
| 5,718,717 A | 2/1998 | Bonutti | |
| 5,725,556 A | 3/1998 | Moser et al. | |
| 5,725,557 A | 3/1998 | Gatturna et al. | |
| 5,733,306 A | 3/1998 | Bonutti | |
| 5,741,276 A | 4/1998 | Poloyko et al. | |
| 5,746,753 A | 5/1998 | Sullivan et al. | |
| 5,749,846 A | 5/1998 | Edwards et al. | |
| 5,752,963 A | 5/1998 | Allard et al. | |
| 5,782,862 A | 7/1998 | Bonutti | |
| 5,782,864 A | 7/1998 | Lizardi | |
| 5,800,445 A | 9/1998 | Ratcliff et al. | |
| 5,807,403 A | 9/1998 | Beyar et al. | |
| 5,810,848 A | 9/1998 | Hayhurst | |
| 5,814,072 A | 9/1998 | Bonutti | |
| 5,830,179 A | 11/1998 | Mikus et al. | |
| 5,830,221 A | 11/1998 | Stein | |
| 5,845,645 A | 12/1998 | Bonutti | |
| 5,846,254 A | 12/1998 | Schulze et al. | |
| 5,861,002 A | 1/1999 | Desai | |
| 5,868,762 A | 2/1999 | Cragg et al. | |
| 5,873,891 A | 2/1999 | Sohn | |
| 5,879,357 A | 3/1999 | Heaton et al. | |
| 5,897,574 A | 4/1999 | Bonutti | |
| 5,899,911 A | 5/1999 | Carter | |
| 5,899,921 A | 5/1999 | Caspari et al. | |
| 5,904,679 A | 5/1999 | Clayman | |
| 5,904,696 A | 5/1999 | Rosenman | |
| 5,908,428 A | 6/1999 | Scirica et al. | |
| 5,919,198 A | 7/1999 | Graves, Jr. et al. | |
| 5,919,202 A | 7/1999 | Yoon | |
| 5,921,986 A | 7/1999 | Bonutti | |
| 5,928,252 A | 7/1999 | Steadman et al. | |
| 5,931,844 A | 8/1999 | Thompson et al. | |
| 5,944,739 A | 8/1999 | Zlock et al. | |
| 5,948,001 A | 9/1999 | Larsen | |
| 5,948,002 A | 9/1999 | Bonutti | |
| 5,954,057 A | 9/1999 | Li | |
| 5,954,747 A | 9/1999 | Clark | |
| 5,964,732 A | 10/1999 | Willard | |
| 5,971,447 A | 10/1999 | Steck, III | |
| 6,010,514 A | 1/2000 | Burney et al. | |
| 6,011,525 A | 1/2000 | Piole | |
| 6,030,393 A | 2/2000 | Corlew | |
| 6,033,413 A | 3/2000 | Mikus et al. | |
| 6,033,430 A | 3/2000 | Bonutti | |
| 6,036,701 A | 3/2000 | Rosenman | |
| 6,048,351 A | 4/2000 | Gordon et al. | |

| | | | | | | |
|---|---|---|---|---|---|---|
| 6,053,908 | A | 4/2000 | Crainich et al. | 6,821,285 | B2 | 11/2004 | Laufer et al. |
| 6,056,722 | A | 5/2000 | Jayaraman | 6,821,291 | B2 | 11/2004 | Bolea et al. |
| 6,056,772 | A | 5/2000 | Bonutti | 6,835,200 | B2 | 12/2004 | Laufer et al. |
| 6,068,648 | A | 5/2000 | Cole et al. | 6,905,475 | B2 | 6/2005 | Hauschild et al. |
| 6,080,167 | A | 6/2000 | Lyell | 6,908,473 | B2 | 6/2005 | Skiba et al. |
| 6,086,608 | A | 7/2000 | Ek et al. | 6,926,732 | B2 | 8/2005 | Derus et al. |
| 6,110,183 | A | 8/2000 | Cope | 6,951,565 | B2 | 10/2005 | Keane et al. |
| 6,117,160 | A | 9/2000 | Bonutti | 6,986,775 | B2 | 1/2006 | Morales et al. |
| 6,117,161 | A | 9/2000 | Li et al. | 6,991,596 | B2 | 1/2006 | Whalen et al. |
| 6,120,539 | A | 9/2000 | Eldridge et al. | 6,991,647 | B2 | 1/2006 | Jadhav |
| 6,139,555 | A | 10/2000 | Hart et al. | 6,997,940 | B2 | 2/2006 | Bonutti |
| RE36,974 | E | 11/2000 | Bonutti | 7,001,327 | B2 | 2/2006 | Whalen et al. |
| 6,143,006 | A | 11/2000 | Chan | 7,011,688 | B2 | 3/2006 | Gryska et al. |
| 6,152,935 | A | 11/2000 | Kammerer et al. | 7,015,253 | B2 | 3/2006 | Escandon et al. |
| 6,159,234 | A | 12/2000 | Bonutti et al. | 7,048,698 | B2 | 5/2006 | Whalen et al. |
| 6,200,329 | B1 | 3/2001 | Fung et al. | 7,048,747 | B2 | 5/2006 | Arcia et al. |
| 6,206,895 | B1 | 3/2001 | Levinson | 7,060,077 | B2 | 6/2006 | Gordon et al. |
| 6,228,096 | B1 | 5/2001 | Marchand | 7,081,126 | B2 | 7/2006 | McDevitt et al. |
| 6,258,124 | B1 | 7/2001 | Darois et al. | 7,083,638 | B2 | 8/2006 | Foerster |
| 6,261,302 | B1 | 7/2001 | Voegele et al. | 7,087,073 | B2 | 8/2006 | Bonutti |
| 6,270,530 | B1 | 8/2001 | Eldridge et al. | 7,089,064 | B2 | 8/2006 | Manker et al. |
| 6,280,460 | B1 | 8/2001 | Bolduc et al. | 7,090,690 | B2 | 8/2006 | Foerster et al. |
| 6,290,711 | B1 | 9/2001 | Caspari et al. | 7,093,601 | B2 | 8/2006 | Manker et al. |
| 6,312,448 | B1 | 11/2001 | Bonutti | 7,105,004 | B2 | 9/2006 | Dicesare et al. |
| 6,319,263 | B1 | 11/2001 | Levinson | 7,108,655 | B2 | 9/2006 | Whalen et al. |
| 6,322,112 | B1 | 11/2001 | Duncan | 7,141,038 | B2 | 11/2006 | Whalen et al. |
| 6,332,889 | B1 | 12/2001 | Sancoff et al. | 7,153,314 | B2 | 12/2006 | Laufer et al. |
| 6,398,795 | B1 | 6/2002 | McAlister et al. | 7,179,225 | B2 | 2/2007 | Shluzas |
| 6,425,900 | B1 | 7/2002 | Knodel et al. | 7,226,558 | B2 | 6/2007 | Nieman et al. |
| 6,428,562 | B2 | 8/2002 | Bonutti | 7,232,448 | B2 | 6/2007 | Battles et al. |
| 6,436,107 | B1 | 8/2002 | Wang et al. | 7,288,063 | B2 | 10/2007 | Petros et al. |
| 6,461,355 | B2 | 10/2002 | Svejkovsky et al. | 7,303,108 | B2 | 12/2007 | Shelton, IV |
| 6,482,235 | B1 | 11/2002 | Lambrecht et al. | 7,320,701 | B2 | 1/2008 | Haut et al. |
| 6,488,691 | B1 | 12/2002 | Carroll et al. | 7,322,974 | B2 | 1/2008 | Swoyer et al. |
| 6,491,707 | B2 | 12/2002 | Makower et al. | 7,326,221 | B2 | 2/2008 | Sakamoto et al. |
| 6,494,888 | B1 | 12/2002 | Laufer et al. | 7,334,822 | B1 | 2/2008 | Hines, Jr. |
| 6,500,195 | B2 | 12/2002 | Bonutti | 7,340,300 | B2 | 3/2008 | Christopherson et al. |
| 6,506,190 | B1 | 1/2003 | Walshe | 7,399,304 | B2 | 7/2008 | Gambale et al. |
| 6,506,196 | B1 | 1/2003 | Laufer | 7,402,166 | B2 | 7/2008 | Fiegl |
| 6,517,569 | B2 | 2/2003 | Mikus et al. | 7,416,554 | B2 | 8/2008 | Lam et al. |
| 6,527,702 | B2 | 3/2003 | Whalen et al. | 7,417,175 | B2 | 8/2008 | Oda et al. |
| 6,527,794 | B1 | 3/2003 | McDevitt et al. | 7,481,771 | B2 | 1/2009 | Fonseca et al. |
| 6,530,932 | B1 | 3/2003 | Swayze et al. | 7,553,317 | B2 | 6/2009 | Weisenburgh, II et al. |
| 6,533,796 | B1 | 3/2003 | Sauer et al. | 7,608,108 | B2 | 10/2009 | Bhatnagar et al. |
| 6,547,725 | B1 | 4/2003 | Paolitto et al. | 7,658,311 | B2 | 2/2010 | Boudreaux |
| 6,551,328 | B2 | 4/2003 | Kortenbach | 7,674,275 | B2 | 3/2010 | Martin et al. |
| 6,551,333 | B2 | 4/2003 | Kuhns et al. | 7,727,248 | B2 | 6/2010 | Smith et al. |
| 6,565,578 | B1 | 5/2003 | Peifer et al. | 7,758,594 | B2 * | 7/2010 | Lamson et al. ............... 606/139 |
| 6,569,187 | B1 | 5/2003 | Bonutti et al. | 2001/0044639 | A1 | 11/2001 | Levinson |
| 6,572,626 | B1 | 6/2003 | Knodel et al. | 2002/0095154 | A1 | 7/2002 | Atkinson et al. |
| 6,572,635 | B1 | 6/2003 | Bonutti | 2002/0107540 | A1 | 8/2002 | Whalen et al. |
| 6,572,653 | B1 | 6/2003 | Simonson | 2002/0128684 | A1 | 9/2002 | Foerster |
| 6,592,609 | B1 | 7/2003 | Bonutti | 2002/0161382 | A1 | 10/2002 | Neisz et al. |
| 6,596,013 | B2 | 7/2003 | Yang et al. | 2002/0193809 | A1 | 12/2002 | Meade |
| 6,626,913 | B1 | 9/2003 | McKinnon et al. | 2003/0109769 | A1 | 6/2003 | Lowery et al. |
| 6,626,916 | B1 | 9/2003 | Yeung et al. | 2003/0191497 | A1 | 10/2003 | Cope |
| 6,626,919 | B1 | 9/2003 | Swanstrom | 2003/0199860 | A1 | 10/2003 | Loeb et al. |
| 6,629,534 | B1 | 10/2003 | St. Goar et al. | 2003/0204195 | A1 | 10/2003 | Keane et al. |
| 6,641,592 | B1 | 11/2003 | Sauer et al. | 2003/0236535 | A1 | 12/2003 | Onuki et al. |
| 6,656,182 | B1 | 12/2003 | Hayhurst | 2004/0030217 | A1 | 2/2004 | Yeung et al. |
| 6,660,023 | B2 | 12/2003 | McDevitt et al. | 2004/0043052 | A1 | 3/2004 | Hunter et al. |
| 6,663,589 | B1 | 12/2003 | Halevy | 2004/0078046 | A1 | 4/2004 | Barzell et al. |
| 6,663,639 | B1 | 12/2003 | Laufer et al. | 2004/0193191 | A1 | 9/2004 | Starksen et al. |
| 6,699,263 | B2 | 3/2004 | Cope | 2004/0193194 | A1 | 9/2004 | Laufer et al. |
| 6,706,047 | B2 | 3/2004 | Trout et al. | 2004/0194790 | A1 | 10/2004 | Laufer et al. |
| 6,709,493 | B2 | 3/2004 | DeGuiseppi et al. | 2004/0243178 | A1 | 12/2004 | Haut et al. |
| 6,715,804 | B2 | 4/2004 | Beers | 2004/0243179 | A1 | 12/2004 | Foerster |
| 6,719,709 | B2 | 4/2004 | Whalen et al. | 2004/0243180 | A1 | 12/2004 | Donnelly |
| 6,730,112 | B2 | 5/2004 | Levinson | 2004/0243227 | A1 | 12/2004 | Starksen et al. |
| 6,736,823 | B2 | 5/2004 | Darois et al. | 2004/0260345 | A1 | 12/2004 | Foerster |
| 6,736,854 | B2 | 5/2004 | Vadurro et al. | 2005/0010203 | A1 | 1/2005 | Edwards et al. |
| 6,740,098 | B2 | 5/2004 | Abrams et al. | 2005/0055087 | A1 | 3/2005 | Starksen |
| 6,767,037 | B2 | 7/2004 | Wenstrom, Jr. | 2005/0065550 | A1 | 3/2005 | Starksen et al. |
| 6,770,076 | B2 | 8/2004 | Foerster | 2005/0107811 | A1 | 5/2005 | Starksen et al. |
| 6,773,438 | B1 | 8/2004 | Knodel et al. | 2005/0107812 | A1 | 5/2005 | Starksen et al. |
| 6,773,441 | B1 | 8/2004 | Laufer et al. | 2005/0154401 | A1 | 7/2005 | Weldon et al. |
| 6,790,213 | B2 | 9/2004 | Cherok et al. | 2005/0165272 | A1 | 7/2005 | Okada et al. |
| 6,802,846 | B2 | 10/2004 | Hauschild et al. | 2005/0177181 | A1 | 8/2005 | Kagan et al. |
| 6,821,282 | B2 | 11/2004 | Perry et al. | 2005/0203344 | A1 | 9/2005 | Orban, III et al. |

| | | | |
|---|---|---|---|
| 2005/0203550 A1 | 9/2005 | Laufer et al. | |
| 2005/0216078 A1 | 9/2005 | Starksen et al. | |
| 2005/0251157 A1* | 11/2005 | Saadat et al. ............ | 606/153 |
| 2005/0267405 A1 | 12/2005 | Shah | |
| 2005/0273138 A1 | 12/2005 | To et al. | |
| 2006/0025750 A1 | 2/2006 | Starksen et al. | |
| 2006/0025784 A1 | 2/2006 | Starksen et al. | |
| 2006/0025789 A1 | 2/2006 | Laufer et al. | |
| 2006/0025819 A1 | 2/2006 | Nobis et al. | |
| 2006/0030884 A1 | 2/2006 | Yeung et al. | |
| 2006/0058817 A1 | 3/2006 | Starksen et al. | |
| 2006/0089646 A1 | 4/2006 | Bonutti | |
| 2006/0167477 A1 | 7/2006 | Arcia et al. | |
| 2006/0265042 A1 | 11/2006 | Catanese, III et al. | |
| 2006/0282081 A1 | 12/2006 | Fanton et al. | |
| 2007/0049929 A1 | 3/2007 | Catanese, III | |
| 2007/0049970 A1 | 3/2007 | Belef et al. | |
| 2007/0060931 A1 | 3/2007 | Hamilton et al. | |
| 2007/0088362 A1 | 4/2007 | Bonutti | |
| 2007/0112385 A1 | 5/2007 | Conlon | |
| 2007/0142846 A1 | 6/2007 | Catanese, III et al. | |
| 2007/0173888 A1 | 7/2007 | Gertner et al. | |
| 2007/0260259 A1 | 11/2007 | Fanton et al. | |
| 2008/0009888 A1 | 1/2008 | Ewers et al. | |
| 2008/0021445 A1 | 1/2008 | Elmouelhi et al. | |
| 2008/0033488 A1 | 2/2008 | Catanese, III et al. | |
| 2008/0039894 A1 | 2/2008 | Catanese, III et al. | |
| 2008/0045978 A1 | 2/2008 | Kuhns et al. | |
| 2008/0058710 A1 | 3/2008 | Wilk | |
| 2008/0065120 A1 | 3/2008 | Zannis et al. | |
| 2008/0082113 A1 | 4/2008 | Bishop et al. | |
| 2008/0086172 A1 | 4/2008 | Martin et al. | |
| 2008/0091220 A1 | 4/2008 | Chu | |
| 2008/0091237 A1 | 4/2008 | Schwartz et al. | |
| 2008/0119874 A1 | 5/2008 | Merves | |
| 2008/0154378 A1 | 6/2008 | Pelo | |
| 2008/0195145 A1 | 8/2008 | Bonutti et al. | |
| 2008/0208220 A1 | 8/2008 | Shiono et al. | |
| 2008/0269737 A1 | 10/2008 | Elmouelhi et al. | |
| 2010/0010631 A1 | 1/2010 | Otte et al. | |
| 2010/0030262 A1 | 2/2010 | McLean et al. | |
| 2010/0114162 A1 | 5/2010 | Bojarski et al. | |
| 2010/0286106 A1 | 11/2010 | Gat et al. | |
| 2010/0286679 A1 | 11/2010 | Hoey et al. | |

FOREIGN PATENT DOCUMENTS

| | | |
|---|---|---|
| EP | 0632999 | 1/1995 |
| EP | 1016377 | 7/2000 |
| EP | 1082941 | 3/2005 |
| EP | 1006909 | 1/2007 |
| EP | 1852071 | 11/2007 |
| EP | 0464480 | 1/2008 |
| EP | 1670361 | 4/2008 |
| EP | 1884198 | 6/2008 |
| EP | 1884199 | 6/2008 |
| EP | 1331886 | 12/2008 |
| FR | 2750031 | 6/1996 |
| JP | 58036559 | 3/1983 |
| RU | 2062121 | 6/1996 |
| RU | 2112571 | 6/1998 |
| RU | 2128012 | 3/1999 |
| RU | 2221501 | 1/2004 |
| SU | 0825094 | 4/1981 |
| WO | WO 92/10142 | 6/1992 |
| WO | WO 93/04727 | 3/1993 |
| WO | WO 93/15664 | 8/1993 |
| WO | WO 0230335 | 4/2002 |
| WO | WO 03/039334 | 5/2003 |
| WO | WO03/077772 | 9/2003 |
| WO | WO2004019787 | 3/2004 |
| WO | WO2004017845 | 4/2004 |
| WO | WO2004030569 | 4/2004 |
| WO | WO2004103189 | 12/2004 |
| WO | WO2007064906 | 6/2007 |
| WO | WO2007053516 | 10/2007 |
| WO | WO2008006084 | 1/2008 |
| WO | WO2008043044 | 4/2008 |
| WO | WO2008443917 | 4/2008 |
| WO | WO2009009617 | 1/2009 |
| WO | WO2010011832 | 1/2010 |

OTHER PUBLICATIONS

Rudolf Hartung, et al., "Instrumentelle Therapie der benignen Prostatahyperplasie", Medizin, Deutsches Arzteblatt 97, Heft 15, Apr. 14, 2000.

Klaus Hofner, et al., "Operative Therapie des benignen Prostatasyndroms", Medizin, Dtsch Arztebl 2007; 104(36):A 2424-9.

R. Hubmann, "Geschichte der transurethralen Prostataeingriffe", Geschichte der Medizin, Urologe [B] 2000 40:152-160.

U. Jonas, et al., "Benigne Prostatahyperplasie", Der Urologe 2006—[Sonderheft] 45:134-144.

O.A. Bacharova, et al., "The Effect of Rhodiolae Rosea Extract on Incidence Rate of Superficial Bladder Carcinoma Relapses", Kozin 1995.

S. Kruck, et al., "Aktuelle Therapiemoglichkeiten des Benignen Prostata-Syndroms", J Urol Urogynakol 2009; 16 (1):19-22.

Osamu Miyake, "Medical Examination and Treatment for BPH", Pharma Med vol. 22, No. 3, 2004, p. 97-103.

Ohashi Teruhisa, "Urinary Dysfunction by Lower Urinary Tract Obstruction in Male", Pharma Medica vol. 8, No. 8, p. 35-39, 1990.

O. Reich, et al. "Benignes Prostatasyndrom (BPS)", Der Urologe A Issue vol. 45, No. 6, Jun. 2006, p. 769-782.

Daito Takashi, "Low-Invasive Treatment for BPH", Medico vol. 34, No. 10, p. 366-369, 2003.

Trapeznikov et al., "New Technologies in the Treatment of Benign Prostatic Hyperplasia", Urologia Nefrol (Mosk) Jul.-Aug. 1996, (4):41-47.

Koyanagi Tomohiko, et al., "Surgery View of 21st Century", Urological Surgery, vol. 84, No. 1, p. 47-53, 2001.

Borzhievski, et al., "Tactics of the Surgical Treatment of Patients With Prostatic Adenoma and Acute Urinary Retention", Urologia Nefrol (Mosk), Jan.-Feb. 1987, (1):39-43.

Sharp, Howard T., M.D., et al., "Instruments and Methods—The 4-S Modification of the Roeder Knot: How to Tie It", Obstetrics & Gynecology, p. 1004-1006, vol. 90, No. 6, Dec. 1997.

P. Schauer et al., "New applications for endoscopy: the emerging field of endoluminal and transgastric bariatric surgery," Surgical Endoscopy, Received Apr. 24, 2006/Accepted Jun. 7, 2006.

Yeung, Jeff, "Treating Urinary Stress Incontinence Without Incision With Endoscopic Suture Anchor and Approximating Device," Aleeva Medical, Inc., 2007.

* cited by examiner

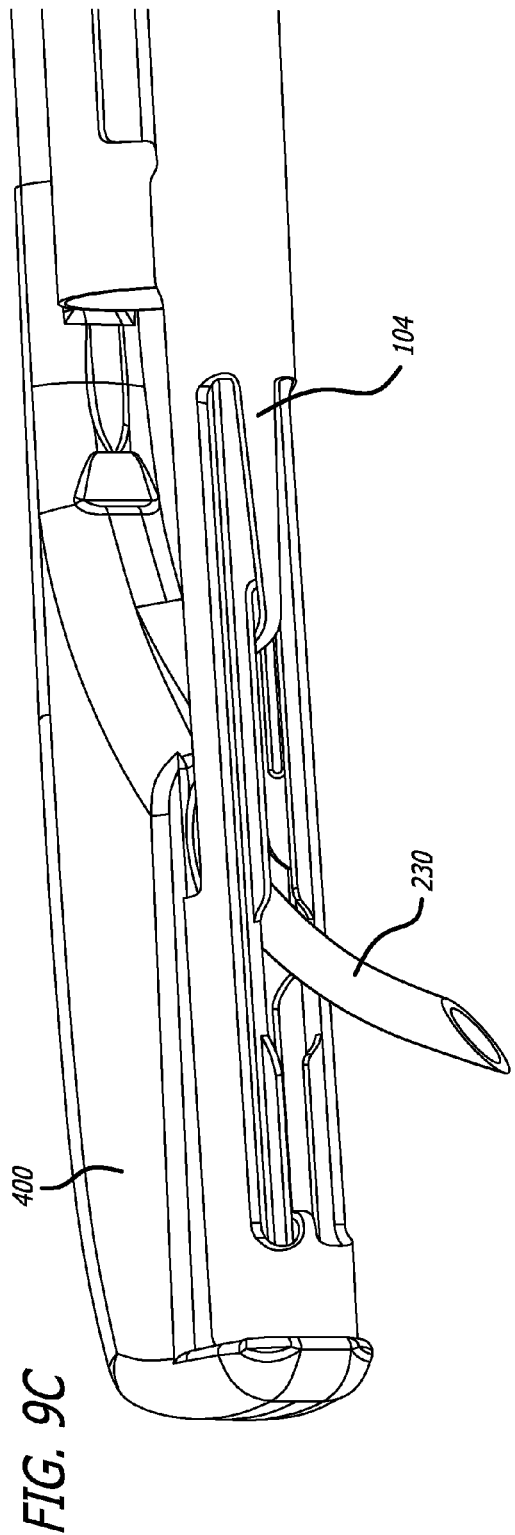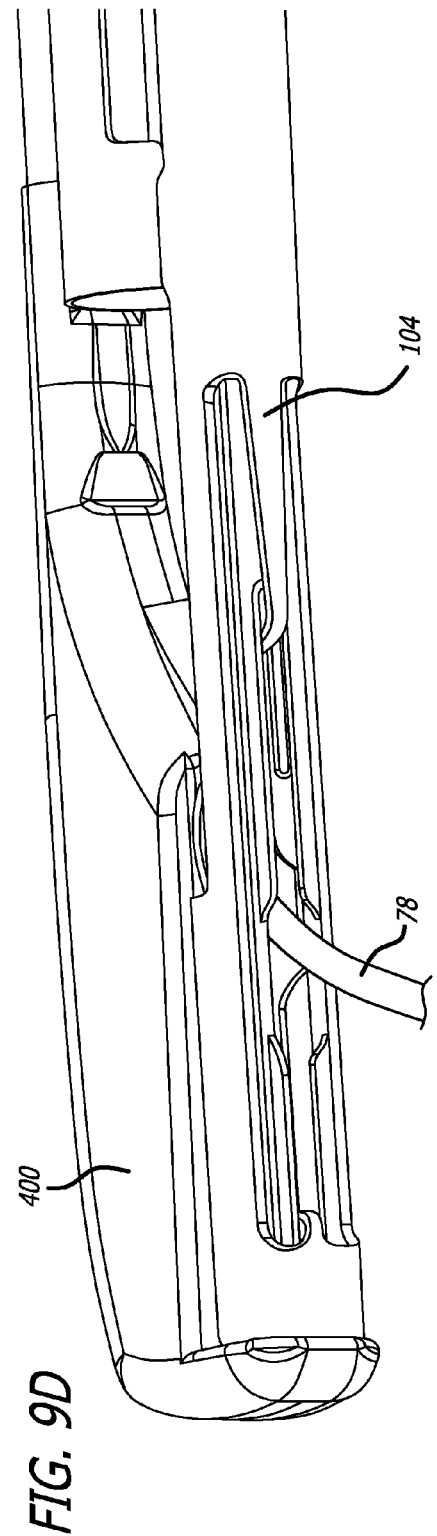

MEDIAN LOBE RETRACTION APPARATUS AND METHOD

CROSS-REFERENCES TO RELATED APPLICATIONS

This application is a continuation-in-part of: 1) U.S. patent application Ser. No. 12/852,243, now U.S. Pat. No. 8,333,776, filed Aug. 6, 2010; 2) U.S. patent application Ser. No. 12/512,674, now U.S. Pat. No. 8,216,254, filed Jul. 30, 2009 which claims the benefit of Provisional Application Ser. No. 61/084,937; 3) U.S. patent application Ser. No. 11/671,914, Now U.S. Pat. No. 8,157,815, filed Jul. 9, 2007: 4) copending U.S. patent application Ser. No. 11/671,914, filed Feb. 6, 2007; 5) U.S. patent application Ser. No. 11/492,690, now U.S. Pat. No. 7,896,891, filed on Jul. 24, 2006; 6) copending U.S. patent application Ser. No. 11/833,660, filed on Aug. 3, 2007, which is a continuation of U.S. patent application Ser. No. 11/318,246, now U.S. Pat. No. 7,645,286, filed on Dec. 20, 2005; and 7) U.S. patent application Ser. No. 11/838,036, now U.S. Pat. No. 7,914,542, filed on Aug. 13, 2007, which is a continuation of U.S. patent application Ser. No. 11/134,870, now U.S. Pat. No. 7,758,594, filed on May 20, 2005; the entire disclosures of each of which are expressly incorporated herein by reference.

FIELD OF THE INVENTION

The present invention relates generally to medical devices and methods, and more particularly to systems and associated methods for manipulating or retracting tissues and anatomical or other structures within the body of human or animal subjects for the purpose of treating diseases or disorders.

One example of a condition where it is desirable to lift, compress or otherwise remove a pathologically enlarged tissue is Benign Prostatic Hyperplasia (BPH). BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

The most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally all device approaches require a urethral catheter placed in the bladder, in some cases for weeks. In some cases catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

There have been advances in developing minimally invasive devices and methods for cosmetic lifting and repositioning of tissues. For example, approaches have been proposed to displace and/or compress lobes of a prostate gland to receive pressure on and provide a less obstructed path through a urethra.

There remains, however, a need for the development of new devices and methods that can be used for various procedures where it is desired to lift, compress, support or reposition the lobes of a prostate. In particular, there is a need for alternative apparatus and treatment approaches for the purpose of manipulating median lobes of a prostate. Various structures ensuring an effective interventional procedure have been found to be needed.

The present disclosure addresses these and other needs.

SUMMARY

Briefly and in general terms, the present invention is directed towards an apparatus and method for deploying an anchor assembly within a patient's body to accomplish retraction or displacement of a lobe of a prostate to lessen obstruction or construction of the urethra. A delivery device is provided to access the anatomy targeted for the interventional procedure, such as a median lobe. The delivery device facilitates the implantation of the anchor assembly in a manner accomplishing retraction or displacement of tissue.

The delivery apparatus of the present disclosure includes various subassemblies which are mobilized via an actuator or other manually accessible structure. The operation of the subassemblies is coordinated and synchronized to ensure accurate and precise implantation of an anchor assembly. In one embodiment, the delivery device is embodied in a tissue approximation assembly.

In one particular aspect, the present invention is directed towards a delivery device which accomplishes the delivery of a first or distal anchor assembly component at a first location within a patient's body and the delivery of a second or proximal anchor assembly component at a second location within the patient. The device also accomplishes imparting tension during delivery to a connector to hold it while attaching the proximal anchor in situ. The procedure can be viewed employing a scope inserted in the device. Also, the delivery device can be sized and shaped to be compatible inside a sheath up to 24F, preferably a 19F sheath or smaller.

The anchor assembly can be configured to accomplish approximating, retracting, lifting, compressing, supporting or repositioning tissue within the body of a human or animal subject. Moreover, the apparatus configured to deploy the anchor assembly as well as the anchor assembly itself are configured to complement and cooperate with body anatomy. Further, the anchor assembly can be coated or imbedded with therapeutic or diagnostic substances, in particular Botulinum toxin, or a silver ion coating or such substances can be introduced into or near an interventional site by the anchor deployment device or other structure.

In various approaches, the anchor can include a distal anchor connected to a proximal anchor by a connector. The distal anchor has a body with a tail. The proximal anchor can include a pair of spaced members which are configured to capture and deform the connector there between and prevent the connector from disengaging from the anchor device once engaged. The mechanism of connector attachment and strength of the assembly is a combination of compression of the connector between deformable structure of the anchor as well as disruption of the connector surface by the anchor. The deformable structure provides surface contact and focuses the compressive forces that cause the connector to conform about the anchor.

Various alternative methods of use are contemplated. The disclosed apparatus can be used to improve flow of a body fluid through a body lumen, modify the size or shape of a body lumen or cavity, treat prostate enlargement, treat urinary incontinence, support or maintain positioning of a tissue, close a tissue wound, organ or graft, perform a cosmetic lifting or repositioning procedure, form anastomotic connections, and/or treat various other disorders where a natural or pathologic tissue or organ is pressing on or interfering with an adjacent anatomical structure. Also, the invention has a myriad of other potential surgical, therapeutic, cosmetic or reconstructive applications, such as where a tissue, organ, graft or other material requires approximately, retracting, lifting, repositioning, compression or support.

In a specific application, the disclosed apparatus are contemplated to be employed to retract or displace a median lobe of a prostate. In one aspect, an anchoring device housed within a delivery device is inserted into a prosthetic urethra transurethrally and the delivery device is employed to compress or displace the median lobe. The anchor is then used to maintain the median lobe in the compressed or displaced configuration. In a related aspect, the delivery device can be equipped with a jaw, lasso or other structure to accomplish the compression or displacement. Further, the system can additionally include an ultrasound or other imaging probe.

In another aspect, the delivery device housing the anchor assembly is first guided into an ejaculatory duct of a patient. The anchor assembly is then deployed from the ejaculatory duct to capture the median lobe so that it can be compressed and/or displaced. In yet a further aspect, an anterior approach can be taken such that tissue on an opposite side of the urethra to that of the median lobe is compressed or displaced to open the urethra.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIGS. 9A-D are side and perspective views, depicting one embodiment of a delivery device and various features thereof;

DETAILED DESCRIPTION OF THE PREFERRED EMBODIMENTS

Turning now to the figures, which are provided by way of example and not limitation, the present disclosure is directed to a device configured to deliver an anchor assembly within a patient's body for treatment purposes. The disclosed apparatus can be employed for various medical purposes including but not limited to retracting, lifting, compressing, approximating, supporting or repositioning tissues, organs, anatomical structures, grafts or other material found within a patient's body. Such tissue manipulation is intended to facilitate the treatment of diseases or disorders such as the displacement, compression and/or retraction of the median lobe of a prostate.

In an aspect of the present invention, one portion of an anchor assembly or implant is positioned and implanted against a first section of anatomy. A second portion of the anchor assembly or implant is then positioned and implanted adjacent to a second section of anatomy for the purpose of retracting, lifting, compressing, approximating, supporting or repositioning the second section of anatomy with respect to the first section of anatomy as well as for the purpose of retracting, lifting, compressing, approximating, supporting or repositioning the first section of anatomy with respect to the second section of anatomy. It is also to be recognized that both a first and second portion of the anchor assembly can be configured to accomplish the desired retracting, lifting, compressing, approximating, supporting or repositioning of anatomy due to tension supplied during delivery via a connector assembly affixed to the first and second portions of the anchor assembly or implant.

With reference to FIGS. 1-4, various features of urological anatomy of a human subject are presented. The prostate gland PG is a walnut-sized muscular gland located adjacent the urinary bladder UB. The urethra UT runs through the prostate gland PG. The prostate gland PG secretes fluid that protects and nourishes sperm. The prostate also contracts during ejaculation of sperm to expel semen and to provide a valve to keep urine out of the semen. A capsule C surrounds the prostate gland PG.

The urinary bladder UB holds urine. The vas deferentia VD define ducts through which semen is carried and the seminal vesicles SV secrete seminal fluid. The rectum R is the end segment of the large intestine and through which waste is dispelled. The urethra UT carries both urine and semen out of the body. Thus, the urethra is connected to the urinary bladder UB and provides a passageway to the vas deferentia VD and seminal vesicles SV.

Further, the trigone T (See FIG. 3) is a smooth triangular region of the bladder. It is sensitive to expansion and signals the brain when the urinary bladder UB is full. The verumontanum VM is a crest in the wall of the urethra UT where the seminal ducts enter. The prostatic urethra is the section of the urethra UT which extends through the prostate.

Figure 1:
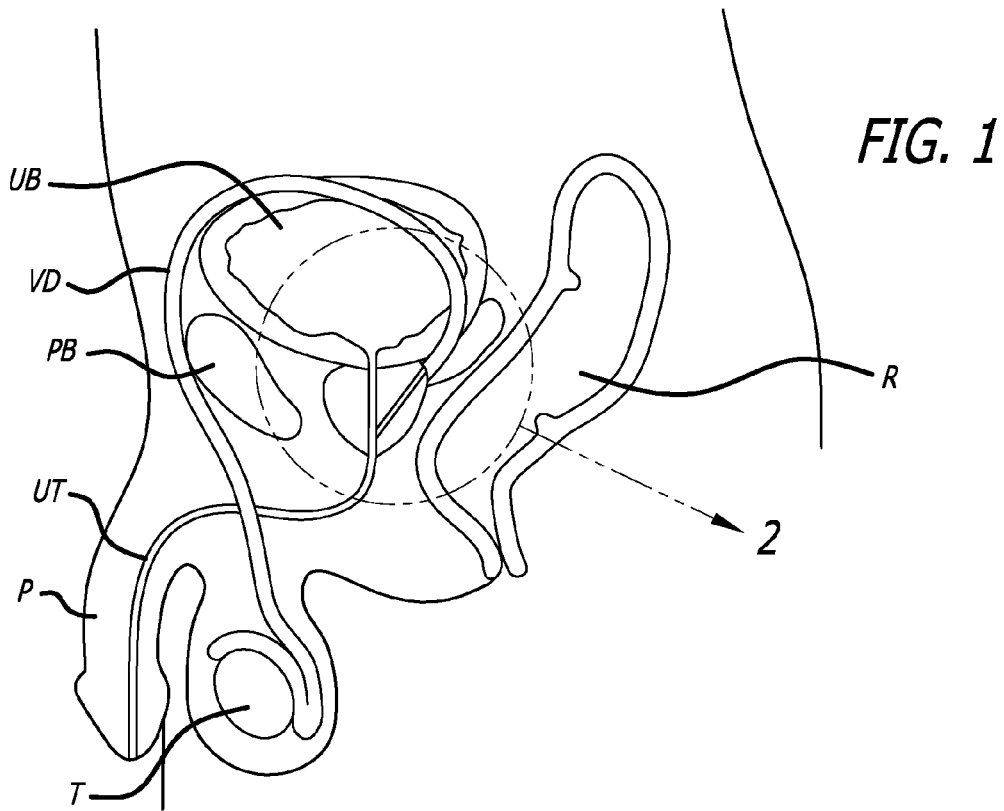
FIG. 1 is a cross-sectional view, depicting anatomy surrounding a prostate in a human subject.
Figure 2:
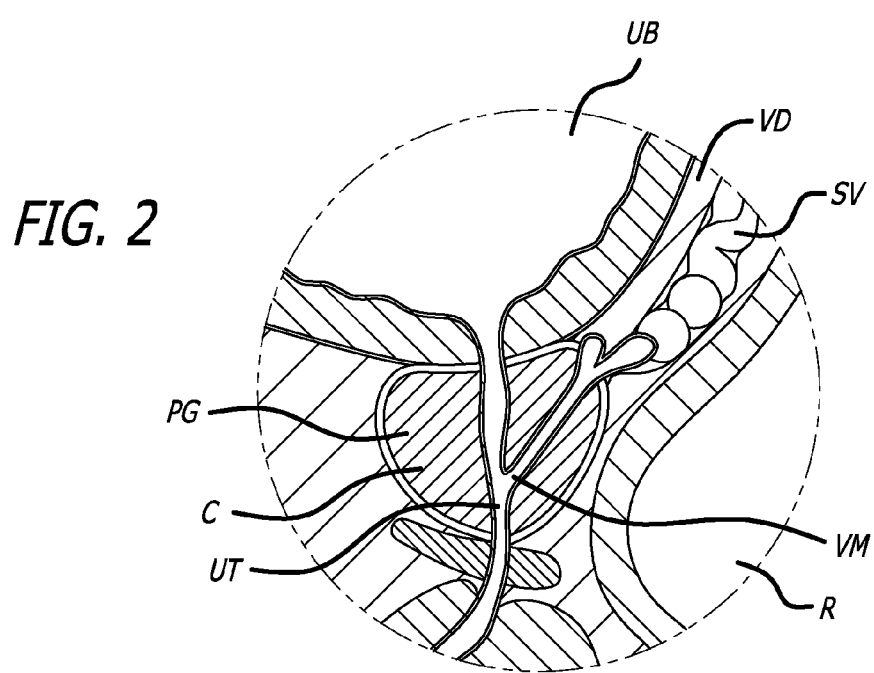
FIG. 2 is an enlarged cross-sectional view, depicting anatomy surrounding a prostate.
Figure 3:
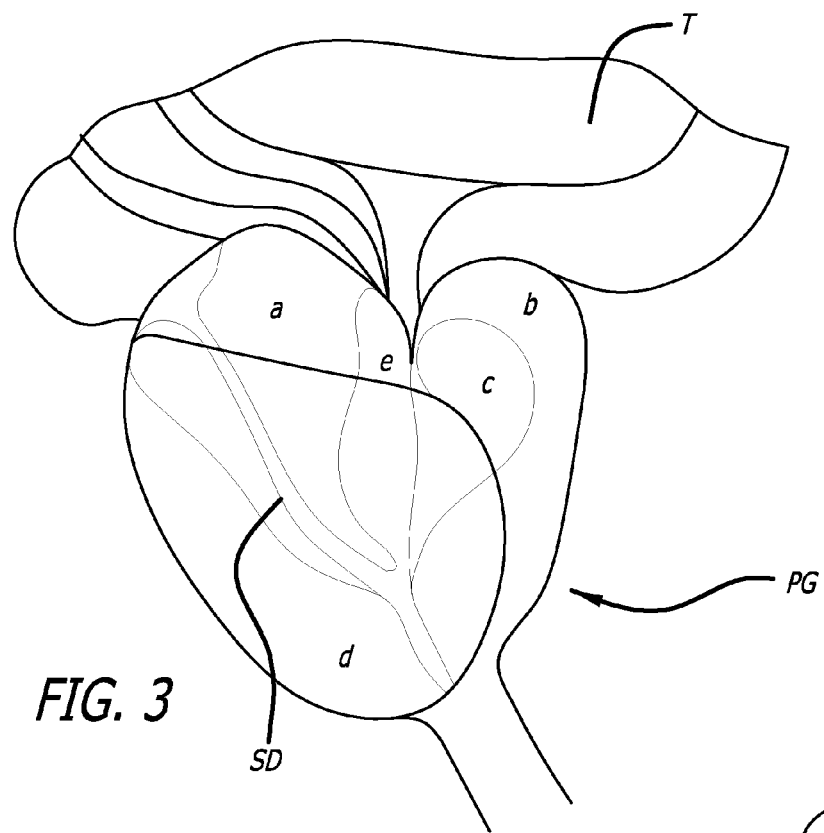
FIG. 3 is a schematic view, depicting prostatic anatomy zones.
Figure 4:
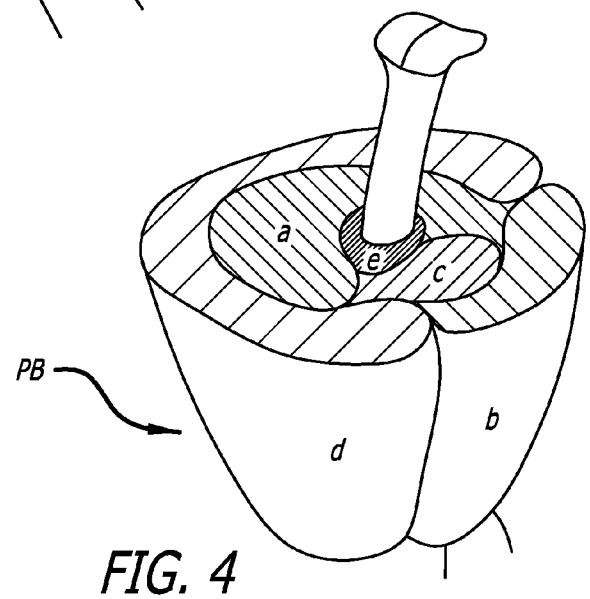
FIG. 4 is a schematic cross-sectional view, depicting further details of the anatomy zones shown in FIG. 3.

The prostate gland can be classified by zones or described by referring to its lobes (See FIG. 4). Whereas the zone classification is typically used in pathology, the lobe classification is more often used in anatomy. The central zone (a) of a prostate gland PG is about 25% of a normal prostate and this zone surrounds the ejaculating ducts. There is some prevalence of benign prostate hyperplasia in the transition zone. The fibromuscular zone (b) is usually devoid of glandular components and as its name suggests, is composed of only muscle and fibrous tissue. The transitional zone (c) generally overlays the proximal urethra and is the region of the gland that grows throughout life. Also, this lobe is often associated with the condition of benign prostatic enlargement. Finally, the peripheral zone (d) is the sub-capsular portion of the posterior aspect of the prostate gland that surrounds the distal urethra.

The lobe characterization is different from the zone characterization, but there is some overlap. The anterior lobe is devoid of glandular tissue and is completely formed of fibromuscular tissue. This lobe thus roughly corresponds to the anterior portion of the transitional zone (c). The posterior lobe roughly corresponds to the peripheral zone (d) and can be palpated through the rectum during a digital rectal exam. The posterior lobe is the site of 70-80% of prostatic cancers. The lateral lobe is the main mass of the prostate and is separated by the urethra. It has been described as spanning all zones. Lastly, the median lobe roughly corresponds to part of the central zone. It varies greatly in size and in some cases is devoid of glandular tissue.

A large or enlarged median lobe can act as a ball valve, blocking the bladder neck or opening into the urethra. Various approaches are contemplated to address such a condition. Thus, it is contemplated that the median lobe can be compressed, displaced and/or retracted to eliminate or decrease the blocking of the bladder neck opening.

Figure 5:
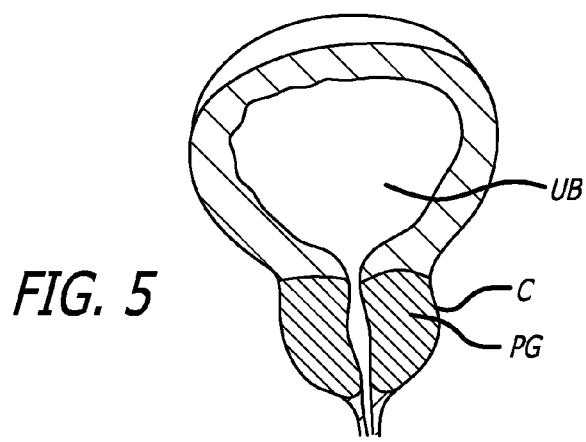
FIG. 5 is a cross-sectional view, depicting a normal prostate.
Figure 6:
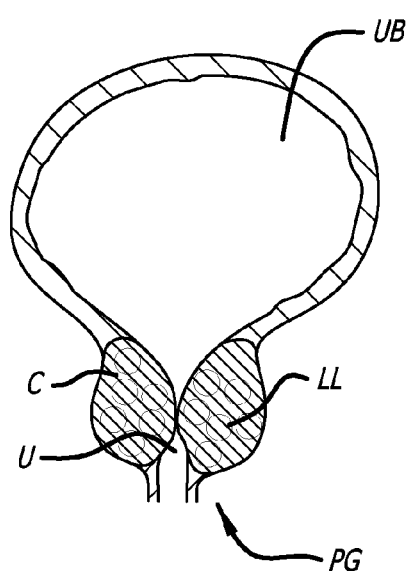
FIG. 6 is a cross-sectional view, depicting a prostate with enlarged lateral lobes.
Figure 7:
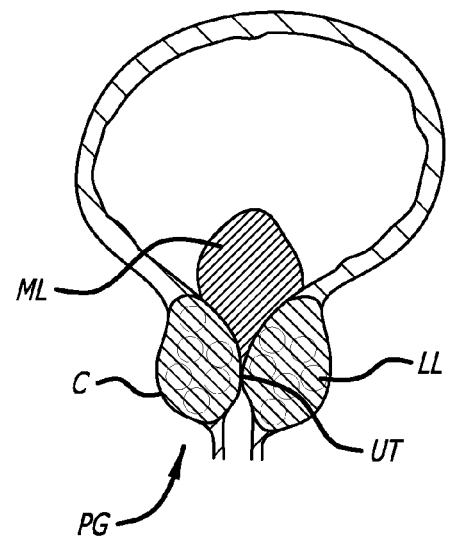
FIG. 7 is a cross-sectional view, depicting a prostate with enlarged lateral lobes and an enlarged median lobe.

Turning now to FIGS. 5-7, there are shown various prostate glands in cross-section. FIG. 5 depicts the urinary bladder UB and prostate gland PG of a healthy subject. FIG. 6 illustrates an individual with a prostate having enlarged lateral lobes LL and FIG. 7 depicts a subject suffering from both enlarged lateral lobes LL and an enlarged median lobe ML. It is to be appreciated that such enlarged anatomy impinges on the urethra UT and affects normal functioning. The following devices and approaches are intended to be employed to free up a path through the prostatic urethra.

Figure 8:
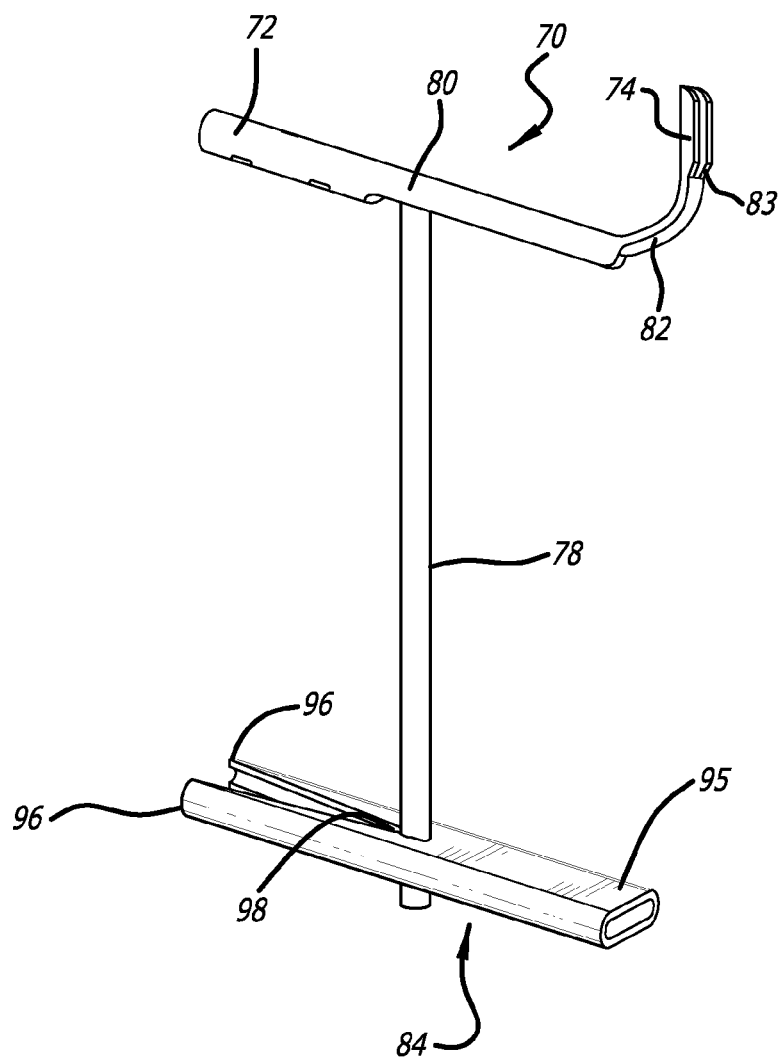
FIG. 8 is a perspective side view, depicting one embodiment of an anchor assembly

In one embodiment (See FIG. 8), the anchor assembly is embodied in a tissue approximation anchor (TAA). The tissue approximation anchor is an implant assembly that includes one tubular member, referred to as the capsular anchor or, more generally, distal anchor 70. The distal anchor 70 is preferably connected by a suture (preferably polyester) 78 to a slotted, flattened-tubular member (preferably comprised of stainless steel), referred to as the urethral anchor or proximal anchor 84. In one specific, non-limiting embodiment, the distal anchor 70 is comprised of an electro-polished Nitinol (nickel titanium alloy SE508, 55.8% nickel) tube.

The tissue approximation anchor is designed to be useable in an office environment (in contrast to requiring a hospital environment) with a delivery tool. The delivery tool is used through a 19 Fr sheath in one preferred embodiment, while in another embodiment a sheath size of 21F is employed. Additionally, the material selection and construction of the tissue approximation anchor still allows for a subsequent TURP procedure to be performed, if necessary, on the prostate. In this suture-based, tissue approximation technique, a needle delivery mechanism is used to implant a nitinol distal anchor 70 and attached suture 78. Once the distal anchor 70 and attached suture 78 have been deployed, with the needle retracted and the suture 78 tensioned, the slotted anchor 84 is pushed by the delivery tool and captures the suture 78 transverse to the anchor axis. The flattened portion of the anchor 84 allows the anchor to be held by the tool without rotating so that it will stay oriented properly to ensure the suture enters the space between the prongs. In many of the illustrated embodiments, the seating region in the slotted anchor for the suture is shown in approximately the midpoint of the slotted anchor but it is within the scope of the present invention to locate the seating region closer to one end or the other of the anchor in order to prevent the ends of the prongs of the anchor from digging into tissue after implantation but rather sit more parallel to the tissue, if so desired.

The nitinol tube can be attached to a USP size 0 PET (Poly Ethylene Terephthalate) monofilament suture 78 by thermally forming the suture to locking features on the anchor 70. Referring again to the suture itself, the PET suture is a round monofilament extrusion/pulltrusion composed of a grade 8816 polyethylene terephthalate. Typically, the base material for the suture is annealed at approximately 375 degrees Fahrenheit for approximately 5 minutes in a straight condition. In one non-limiting embodiment, the PET suture 78 has a diameter of 0.015 inches and a tensile strength greater than or equal to 12.7 pounds. It is preferred that the tensile strength be about 6 pounds or greater.

In one embodiment, the proximal anchor 84 is a 316L stainless steel flattened tube that is slotted, electro-polished, and passivated. The anchor is depicted in the figures with a flat surface on the top or bottom but it is within the scope of the present invention that only one of the surfaces be flat and that the surface(s) do not have to be true flat but rather could have a slight dip or protrusion on the flattened surfaces. The slotted anchor 84 includes prongs 96 that grip and deform the suture 78 in the seating region 98 between the spaced prongs 96. It is to be recognized that rather than defining mirrored images, in one or more of the embodiments disclosed herein, the seating region can be formed by staggered structure or one prong can have a longer area defining seating structure than an opposing prong to provide an effective engagement for a particular suture or connector design. The prongs 96 are quite stiff and robust therefore subject to minimal to no deflection. In particular preferred embodiments, the prongs or overall width of the anchor adjacent the seating region 98 expands, after a connector has been seated in the seating region, less than about 0.002 inches (i.e., less than about five percent), more preferably less than about 0.001 inches (i.e., less than about two and half percent). In particular preferred embodiments, the prongs or overall width of the anchor adjacent the ends of the prongs 96 expands, after a connector has been seated in the seating region, less than about 0.0065 inches (i.e., less than about seventeen percent), more preferably less than about 0.006 inches (i.e., less than about fifteen percent). Due to its particular configuration, the slotted anchor 84 also requires less force to deploy onto a suture 78. Being relatively stiff, the prongs 96 of the slotted anchor 84 are significantly more resistant to bending. The four individual edges/faces (two on each prong 96) of the slotted anchor 84 disrupt the surface of the suture 78, both biting into the suture 78 as well as compressing the suture 78 between the slotted prongs 96, including sometimes melting the suture locally due to the pressure and heat created during deployment of the slotted anchor onto the suture. The reduced area of contact provided by this structure as well as multiple planes of engagement of the anchor slot to the connector strengthens connections and prevents inadvertent separation. Additionally, the narrow width between the prongs 96 is substantially smaller than the connector diameter, with the purpose to allow the stiffer prongs to slightly elastically expand over the connector and contribute to anchor retention by means of compression but not intended to receive the connector into this relief slot, which is positioned proximal to the seating portion 98. It is beneficial in some circumstances however for the slotted anchor to be pushed far enough on to the connector such that the connector becomes at least partially seated in the slot inception relief slot so that it becomes pinched and/or wedged. In this circumstance, a two-part compression slot is created wherein the short, narrow part of the slot ensures a good mechanical interlock but may compromise the strength of the suture locally and the second wider part is ensures a good mechanical interlock but without any compromise in the strength of the suture. Notably, the outwardly stepped slot width also has a dimension smaller than the connector diameter, and receives the connector with some interference.

The prongs 96 can be formed from a wide (or flattened) tubular structure. The wider and smoother prongs 96 of the anchor 84 assist in preventing the prongs 96 from irritating and/or damaging tissue, which is more likely to occur with a thinner and pointier leg structure. Further, in one embodiment, the slot in the anchor 84 is configured to create registering and aligning surfaces to the delivery tool (not shown). In several embodiments, the two inner surfaces of the prongs 96 of the slotted anchor 84 are configured as corresponding inwardly facing U-shapes. In this configuration, the inner surfaces of the prongs 96 bite into the suture 78. In still other embodiments, the two inner surfaces of the prongs 96 of the slotted anchor 84 are configured to present a notched geometry. In still other embodiments, the inner surfaces of the prongs are configured with burrs, roughened edges, serrations, etc. to enhance their ability to retain the connector.

Referring now to FIGS. 9A-D, there is shown one embodiment of a delivery device 100. This device is configured to include structure that is capable of both gaining access to an interventional site as well as assembling and implanting one or more anchor assemblies or implants within a patient's body. The delivery device 100 can be configured to assemble and implant a single anchor assembly or implant. The device is further contemplated to be compatible for use with a 19F sheath. The device additionally includes structure configured to receive a conventional remote viewing device (e.g., an endoscope) so that the steps being performed at the interventional site can be observed.

Prior to use of the present device 100, a patient typically undergoes a five day regiment of antibiotics. A local anesthesia can be employed for the interventional procedure. A combination of an oral analgesic with a sedative or hypnotic component can be ingested by the patient. Moreover, topical anesthesia such as lidocaine liquids or gel can be applied to the bladder and urethra.

The anchor delivery device 100 includes a handle assembly 102 connected to an elongate tissue access assembly 104. The elongate tissue access assembly 104 houses components employed to construct an anchor assembly and is sized to fit into a 19F cystosopic sheath for patient tolerance during a procedure in which the patient is awake rather than under general anesthesia. The tissue access assembly is stiff to allow manual compression of tissue at an interventional site by leveraging or pushing the handle assembly 102.

The anchor delivery device 100 further includes a number of subassemblies. A handle case assembly 106 including mating handle parts which form part of the handle assembly 102. The handle assembly 102 is sized and shaped to fit comfortably within an operator's hand and can be formed from conventional materials. Windows can be formed in the handle case assembly 106 to provide access to internal mechanisms of the device so that a manual override is available to the operator in the event the interventional procedure needs to be abandoned.

In one embodiment, the delivery device 100 is equipped with various activatable members which facilitate assembly and delivery of an anchor assembly at an interventional site. A needle actuator 108 is provided and as described in detail below, effectuates the advancement of a needle assembly (loaded with a first component of an anchor assembly) to an interventional site. In a preferred embodiment, the needle assembly has a needle that moves through a curved trajectory and exits the needle housing in alignment with a handle element, and in particular embodiments, in alignment with the grip. In various other embodiments, the needle housing is oriented such that the needles exits the housing at either the two o'clock or ten o'clock positions relative to a handle grip that is vertical. A needle retraction lever assembly 110 is also provided and when actuated causes the needle assembly to be withdrawn and expose the first anchor component. This action and the structure involved is also described in detail below. Finally, the delivery device 100 is equipped with a rear or proximal anchor actuator assembly 112 which as fully described below, upon actuation, accomplishes assembly of a second component to the anchor assembly and release of the anchor assembly at the interventional site.

In one particular, non-limiting use in treating a prostate, the elongate tissue access portion 104 of a delivery device is placed within a urethra (UT) leading to a urinary bladder (UB) of a patient. In one approach, the delivery device can be placed within an introducer sheath (not shown) previously positioned in the urethra or alternatively, the delivery device can be inserted directly within the urethra. When employing an introducer sheath, the sheath can be attached to a sheath mount assembly (described below). The patient is positioned in lithotomy. The elongate portion 104 is advanced within the patient until a leading end thereof reaches a prostate gland (PG). In a specific approach, the side(s) (i.e., lobe(s)) of the prostate to be treated is chosen while the device extends through the bladder and the device is turned accordingly. The distal end of the elongate portion can be used to depress the urethra into the prostate gland by compressing the inner prostate tissue. The inside of the prostate gland (i.e., adenoma) is spongy and compressible and the outer surface (i.e., capsule) of the prostate gland is firm. By the physician viewing with an endoscope, he/she can depress the urethra into the prostate gland compressing the adenoma and creating the desired opening through the urethra. To accomplish this, the physician rotates the tool. The physician then pivots the tool laterally about the pubic symphysis PS relative to the patient's midline.

Figure 9A:
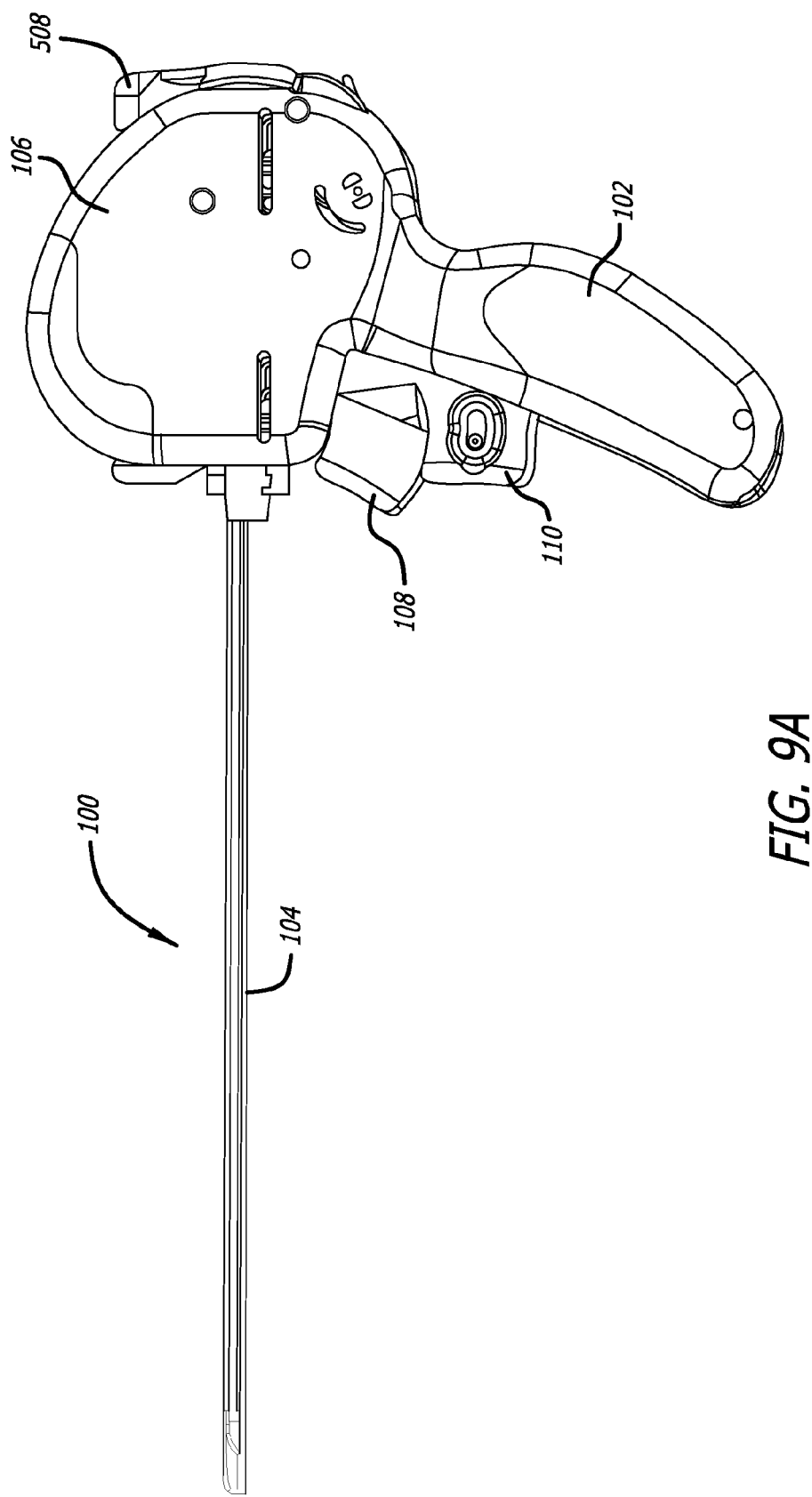
Figure 9B:
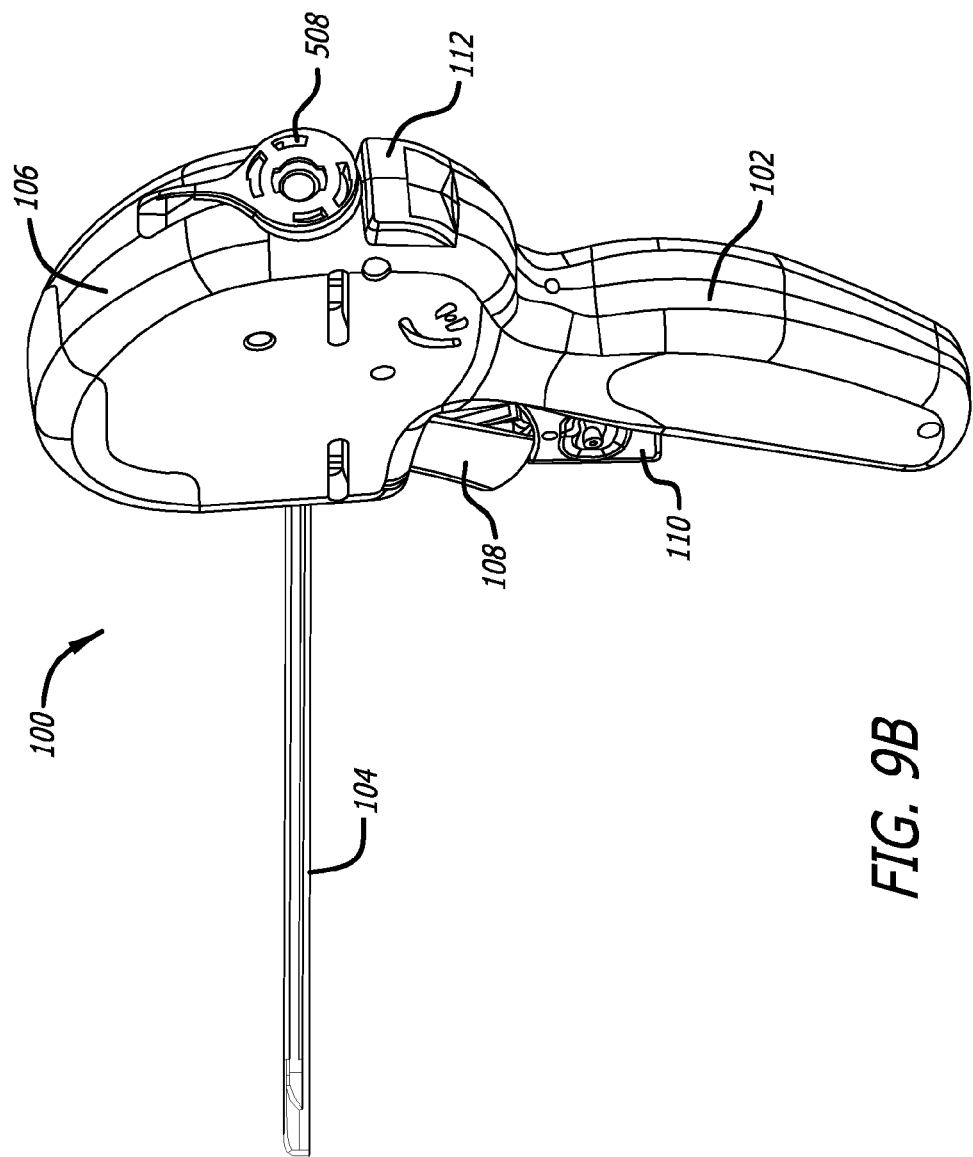

As shown in FIGS. 9A-B, the delivery device is at this stage configured in a ready state. The needle actuator 108 and the needle retracting lever 110 are in an inactivated position.

Upon depression of the needle actuator 108, the needle assembly 230 is advanced from within the elongate member 104 (See FIG. 9C). The needle assembly can be configured so that it curves back toward the handle as it is ejected. In use in a prostate intervention, the needle assembly is advanced through and beyond a prostate gland (PG). Spring deployment helps to ensure the needle passes swiftly through the tough outer capsule of the prostate without "tenting" the capsule or failing to pierce the capsule. In one approach, the needle is made from Nitinol tubing and can be coated with Parylene N. Such a coating helps compensate for frictional or environmental losses (i.e. wetness) which may degrade effectiveness of needle penetration.

After complete depression of the needle actuator 108 and the unlocking of the needle retraction lever 110, the needle retraction lever 110 can be actuated. Such action results in a withdrawal of the needle assembly 230, leaving the connector 78 of an anchor assembly in an extended position (See FIG. 9D). In one embodiment, the needle 230 is withdrawn further than its original position within the device pre-deployment. In a prostatic interventional procedure, this action can result in delivering a first or distal anchor component attached to the connector 78 beyond an outer surface of a prostate gland (PG) with the connector 78 within a penetration tract in the prostate gland extending toward the terminal end 400 of a delivery device.

The proximal anchor actuator assembly 112 is configured at a back end of the casing 106. Actuation of the proximal anchor actuator 112 results in causing the proximal anchor component 84 to engage the connector 78. It also accomplishes cutting a connector 78 to length. Within a patient's body, the anchor assembly is configured across anatomy within the interventional site. The urethra (UT) is thus widened due to the anchor assembly compressing the surrounding enlarged prostate tissue due to the fact that the outer capsular tissue is rather strong, substantially non-compressible and non-displaceable while the adenoma of the prostate gland is compressible and the urethral wall displaceable.

Figure 10A:
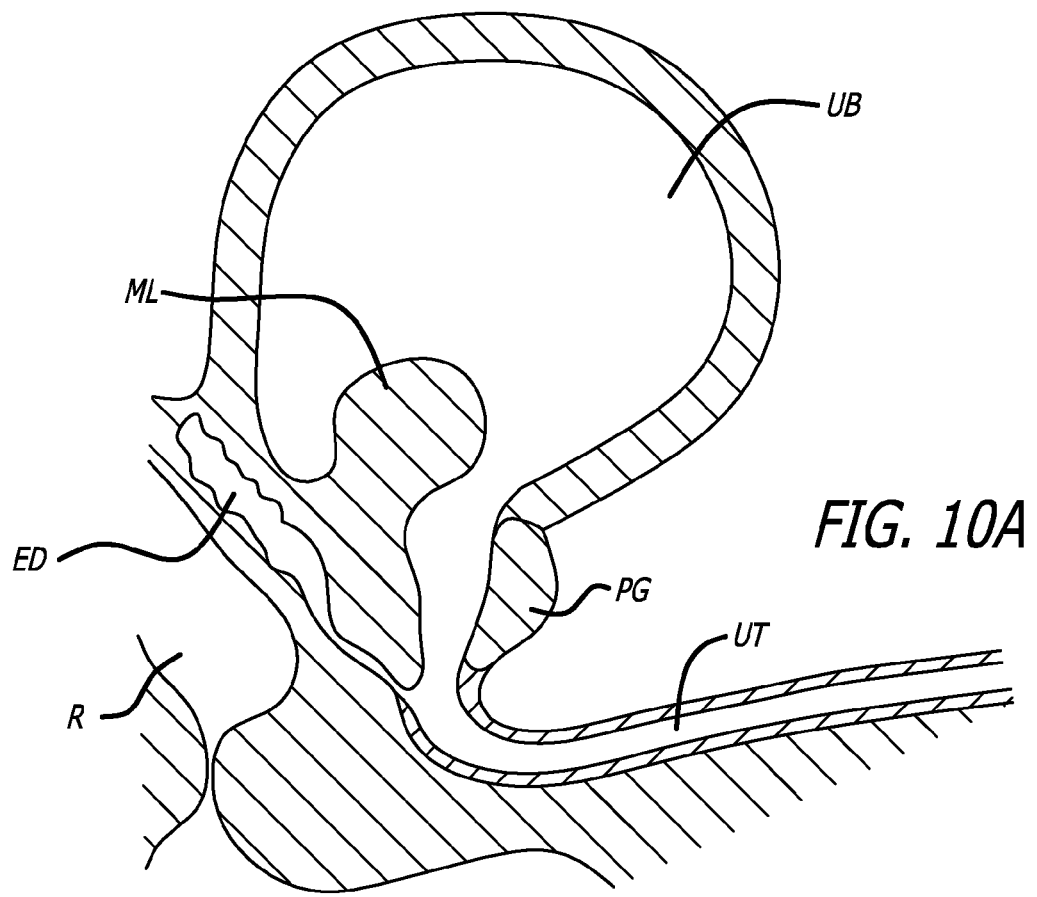
FIGS. 10A-N are various cross-sectional views, depicting details of an approach to compressing and displacing a median prostate lobe of a prostate.
Figure 10B:
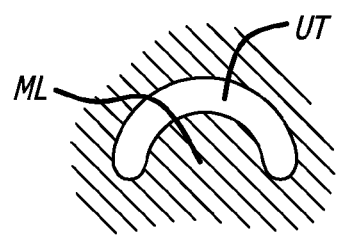

Turning now to FIGS. 10A-I, an approach to treating patients with median lobe ML disease is presented. Such an approach can be used as a complementary therapy with separate treatments for lateral lobes or can be employed to solely treat a median lobe ML. Because an enlarged median lobe ML can extend into the urinary bladder UB and may act as a ball valve interfering with normal function (See FIGS. 10A and 10B; FIG. 10B is a view through the prostatic urethra and into the urinary bladder), special consideration to moving tissue away from a ball valve location may facilitate accomplishing optimal results. The purpose here being to provide a less invasive means to treat median lobe hypertrophy as compared to TURP and TUIP (transurethral incision of the prostate). By avoiding such invasive approaches, there is minimal risk of disrupting the smooth muscle of the bladder neck and nerve tissue, and ejaculating function and continence complications will likely be lower. BPH is a very prevalent disease that dramatically affects the quality of life of older men. About 30% of these men have a median lobe that creates a ball-valve effect. The presently disclosed procedure can significantly improve the urinary symptoms of these patients with a much better side effect profile. However, certain previously contemplated procedures currently require patient screening in order to exclude some patients with median lobes requiring treatment because these patients do not respond as readily to the therapy. Because current medical therapy may not be effective on median lobes, these patients only have resection/ablation as available options which both carry significant side effects. The invention treats patients with median lobes without the significant side effect profile due to resection or ablation. The invention preserves the tissue of the prostrate, thus preserving the prostate functions.

Accordingly, an approach involving inserting a tissue suturing or anchoring device into the prostatic urethra UT transurethrally to compress and/or displace the median lobe ML is contemplated. Once the lobe is compressed or displaced, tissue anchors are advanced in a specific direction to maintain the compression/displacement of the median lobe.

Figure 10C:
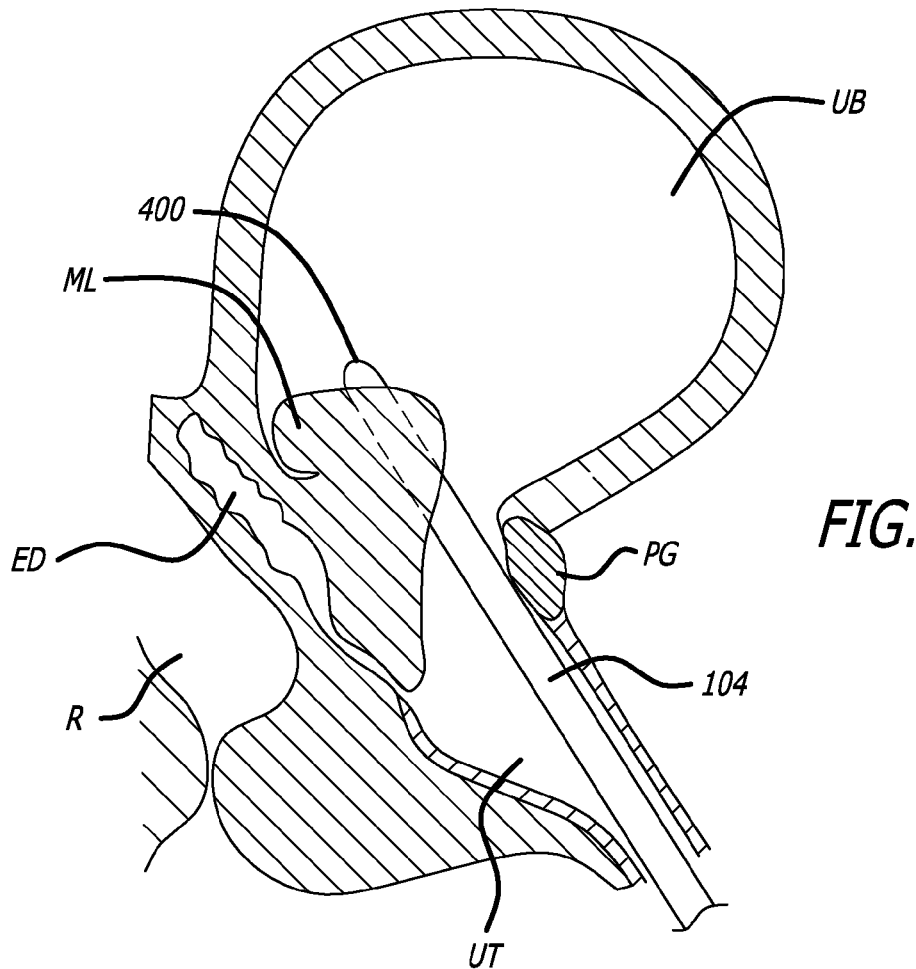
Figure 10D:
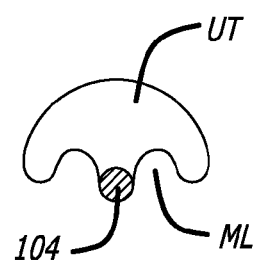

As an initial step, sagittal views of a patient's bladder and prostate can be taken using transabdominal or transrectal ultrasonography. In this way, the patient's anatomy can be assessed. In this regard, an intravesical prostate measurement is taken to determine the vertical distance from a tip of the median lobe protrusion to the base of the bladder. As shown in FIGS. 10C-D, after assessing the anatomy, the elongate tissue access assembly 104 of an anchor delivery device (See FIGS. 9A-B) is advanced within the urethra UT and into apposition with the median lobe ML. FIG. 10D is a view through the urethra UT depicting the compression and displacement of the median lobe ML.

One specific series of actions is to position the tissue access assembly 104 so that its terminal end 400 is anterior to a prominent portion of the median lobe ML and then displace the surface in the posterior direction to move the median lobe ML away from a centerline of the urethra lumen UT. The median lobe consequently forms a tissue fold (See FIG. 10D) about the delivery instrument.

Figure 10E:
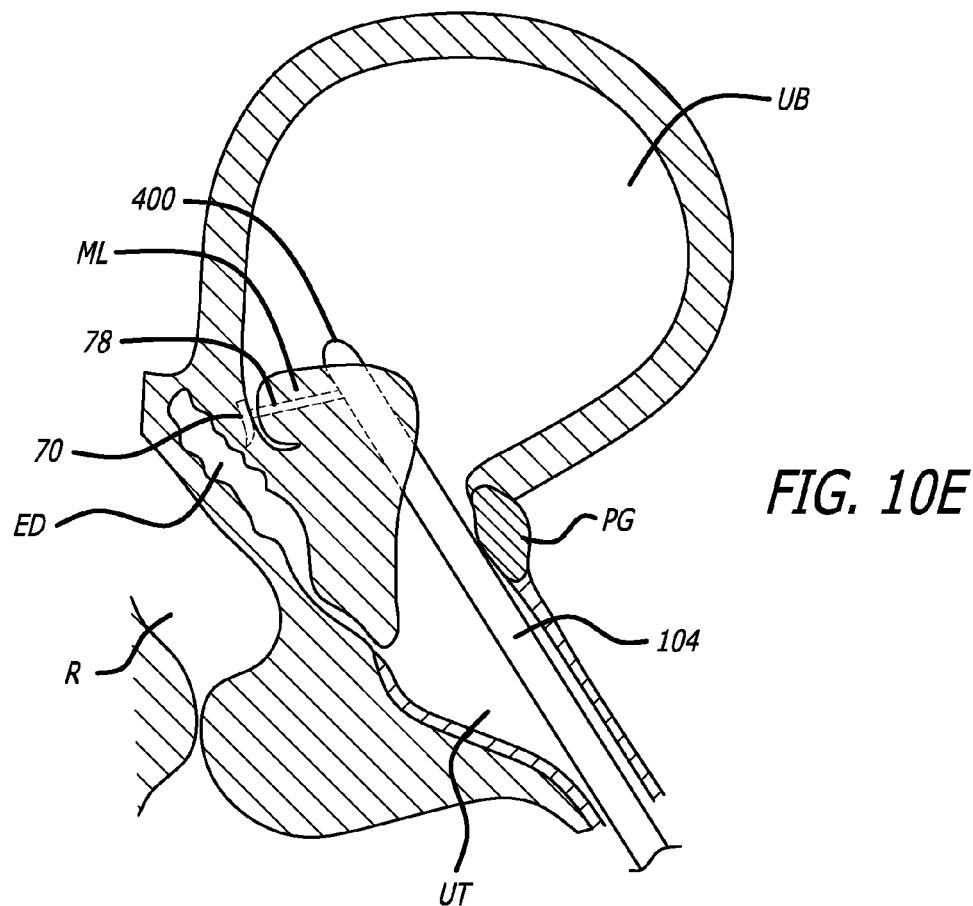
Figure 10F:
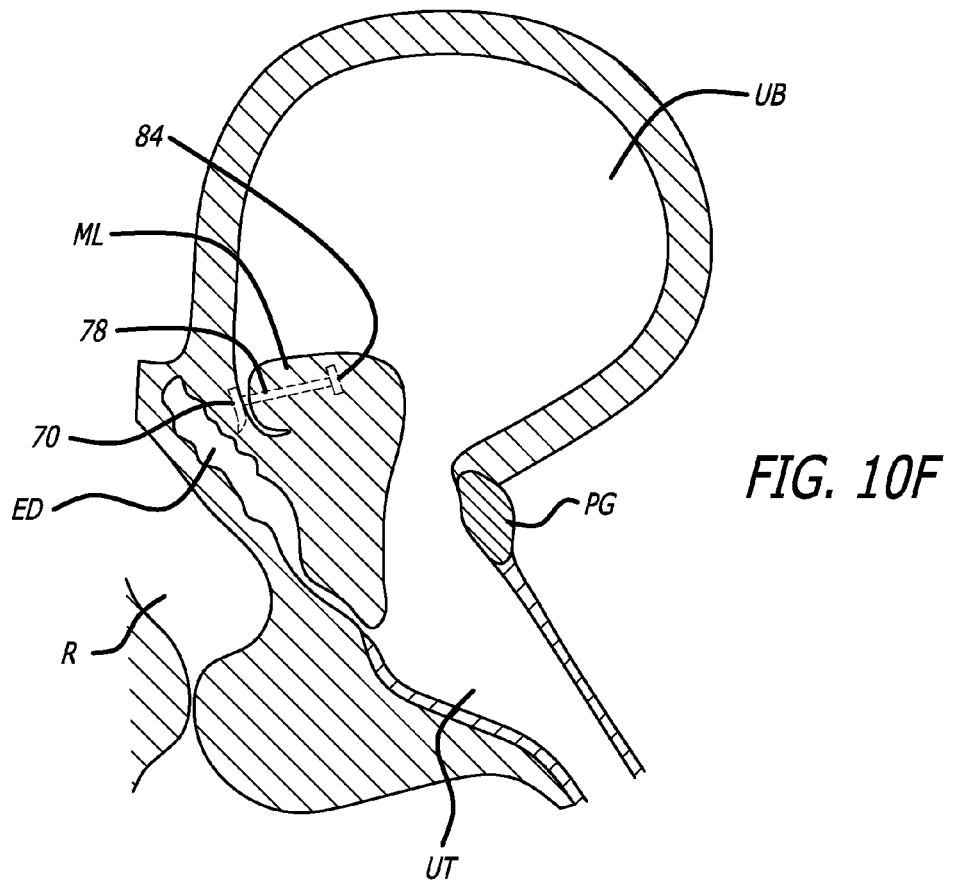
Figure 10G:
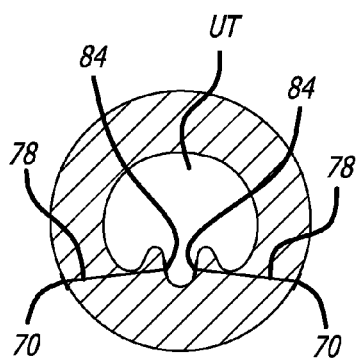
Figure 10H:
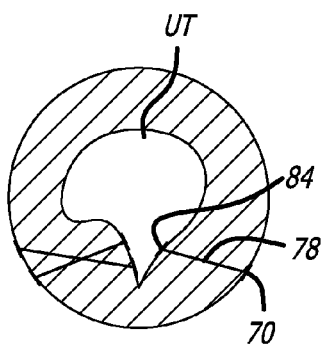
Figure 10I:
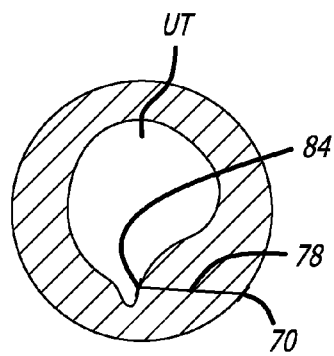
Figure 10J:
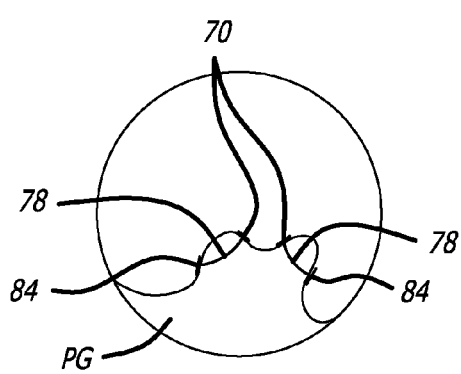
Figure 10K:
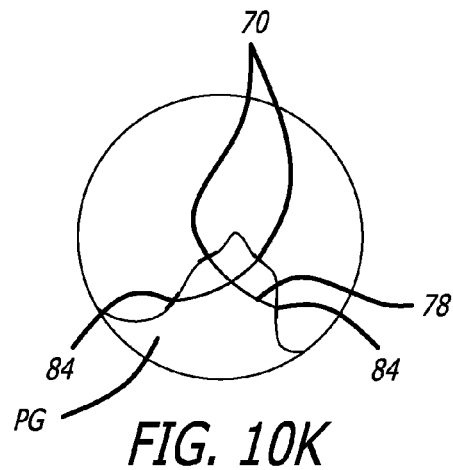

Next, an anchor assembly can be deployed in a generally lateral direction to hold the median lobe ML in the compressed and displaced state to accomplish desired retraction (See FIG. 10E-F). As described above, the anchor delivery device accomplishes first deploying a distal anchor 70 through and beyond the median lobe ML and then assembles and attaches a proximal anchor component 84 onto a connector 78. The distal anchor 70 is implanted in anatomy having sufficient purchase. The proximal anchor 84 is placed against the median lobe ML in a manner to make the tissue fold a permanent canal through the median lobe ML.

In an alternative approach, two or more anchors can be deployed and implanted to create a net 6 o'clock net force displacement. For example, two anchors can be implanted at 5 and 7 o'clock to exert a shared or net force displacement in a 6 o'clock direction.

As shown in FIGS. 10G-K which depict views of compressed median lobes ML through the urethra UT, various tissue deflection directions and multiple anchor deployment arrangements, crossing and otherwise, can be used. For example, 2-4 o'clock or 8-10 o'clock directions are contemplated as are other orientations. Moreover, deflecting posterior—laterally and then deploying the anchor towards the same side as a lateral direction, for example, is also contemplated.

Figure 10L:
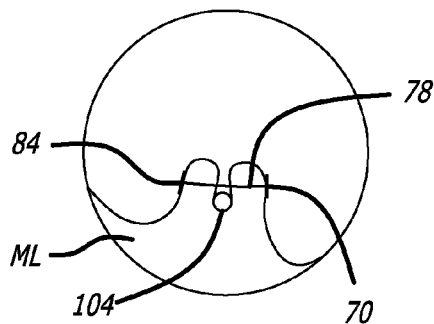
Figure 10M:
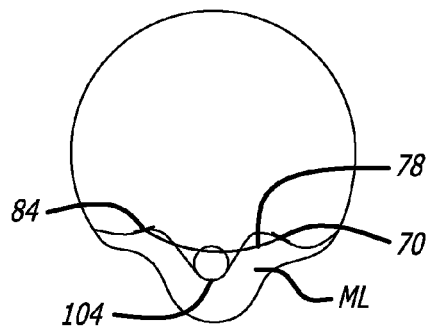

With specific reference to FIGS. 10L and M, an external tool 104 is used to deflect and move the median lobe ML before an anchor assembly is deployed to contain the median lobe ML in a new position which reduces the cross sectional area of the target tissue. A first approach (FIG. 10L) involves reducing the cross section of the median lobe ML by pushing down on the median lobe causing the median lobe to fold in on to itself. A second approach (FIG. 10M) involves pressing the median lobe ML and displacing the median lobe such that the capsule of the prostate has been displaced. In both scenarios, an anchor assembly or other mechanism is used to mechanically constrain the new position of the median lobe. Upon attaching this mechanism, the external tool used to deflect the median lobe ML is removed. This approach is not limited to pressing in a downward direction. Rather, this approach may be performed by pressing in any direction to deflect the median lobe in a new location prior to constraining.

Figure 10N:
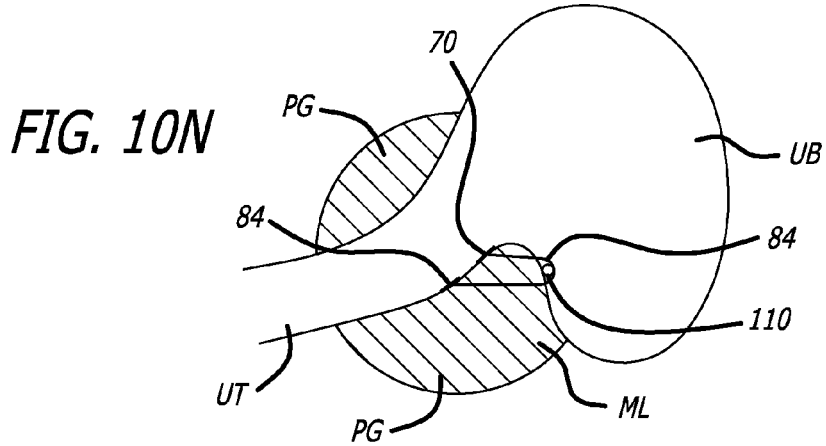

In still yet another approach (See FIG. 10N), an anchor device can be looped through the median lobe ML. As before, a transurethral approach can be taken to access the prostate PB and deliver the anchor. During delivery, tension could be applied to a distal end of the connector 78 to rotate the median lobe ML and clear any obstruction. A rigid element such as a pin 110 may be used to provide a more rigid surface around which the connector 78 is looped to provide a larger displacement effect.

In an alternate approach, a device having a jaw-shaped tip (not shown) that grabs the distal half of the median lobe just distal to the bladder trigone can be used for median lobe ML retraction. As before, the needle is advanced across the median lobe in a predetermined curved horizontal trajectory and leaves a connector 78 behind it. The connector 78 maintains the median lobe ML in the compressed configuration, which then opens up the bladder neck to allow urine to pass around the sides in the created channel. Thus, the bladder neck is opened just enough to allow urine to pass through, negating much of the median lobe ball-valve effect. The prostate is usually slow-growing at this point so the result should be durable. This approach does not involve any ablation or removal of tissue, and should not carry the same side effect profile as ablative-resection therapies.

In a related approach, instead of having the connector go through the median lobe, a suture is extended out and the surgeon lassos the median lobe. The lasso-suture is then tightened which functions to squeeze/compress the median lobe, thus achieving the same effect of opening the bladder neck. The suture, instead of going horizontally through the median lobe, can be directed posteriorly which compresses and flattens the lobe, opening up the anterior aspect of the bladder neck. The suture can be made of a dissolvable polymer. One can also create multiple holes in the median lobe that are held open with sutures. If an implant is used, a web-shaped spacer (not shown) can be placed between the median lobe and the sides of the bladder neck where the two structures would have opposed. This would prevent the ball-valve effect by allowing urine to drain through the spacer.

Figure 11A:
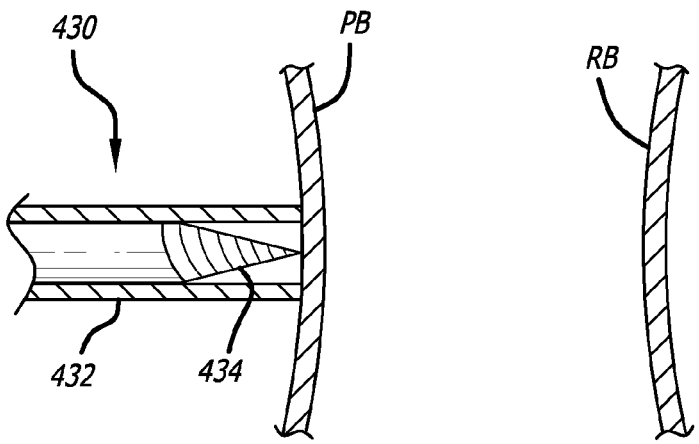
FIGS. 11A-C are partial cross-sectional views, depicting an alternative needle assembly approaches.
Figure 11B:
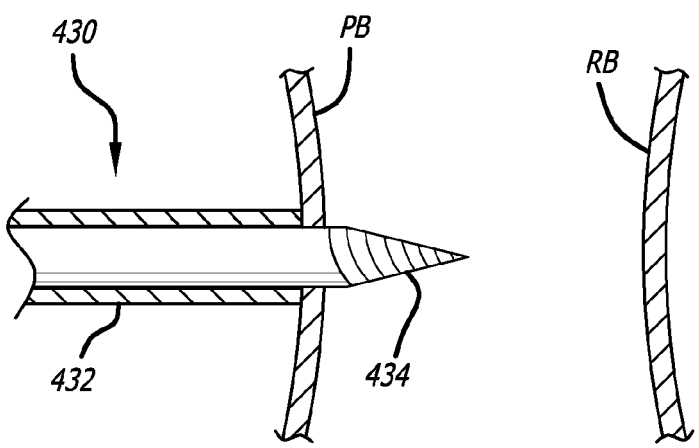

Additionally, in yet another approach, the anchor delivery device can be equipped with a blunt needle assembly 430 designed to stop its penetration at the prostate boundary PB (See FIGS. 11A-B). Such a needle can be useful in applications specific to the treatment of median lobes in that penetration beyond the prostatic boundary PB and into the rectum wall boundary RB can be avoided.

Figure 11C:
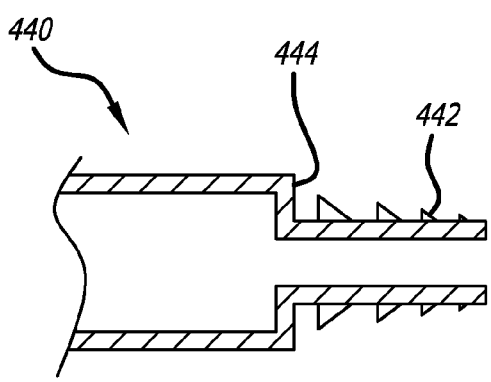

The needle assembly 430 can include a blunt hollow needle 432 which contains a telescoping self-tapping screw head 434. Once the blunt hollow needle 432 reaches the prostate boundary PB, the screw head 434 is deployed, the screw head acting much like a self-tapping screw. Rotation of the screw head 434 accomplishes engagement with the prostatic boundary PB and punctures a hole in the wall. The relative depth of the penetration is tightly controlled which prevents for example, penetrating into the rectum. The penetration method is relatively slow and well controlled so that consistent penetration can be achieved. In yet another alternative approach (FIG. 11C), a needle assembly 440 can include an outer surface equipped with self-tapping thread structure 442. A stop 444 is further provided to control depth of insertion.

It is further contemplated that retraction of the median lobe can be accomplished using a transrectal needle device that can be inserted into the needle lumen of a TRUS (trans rectal ultrasound) probe. The needle is advanced through the median lobe of the prostate into the prostatic urethra using real-time ultrasound guidance or using baseline ultrasound data to select the device size, deployment depth, and/or deployment direction. The needle is used to deploy an anchor assembly to compress or displace the median lobe. After needle access to the prostatic urethra through the median lobe, a urethral end of the connector is deployed. As the needle is retracted, the urethral end of the anchor assembly seats on the prostatic urethra and then tension is applied to the anchor thereby compressing or displacing the median lobe. At a predetermined distance, a second end of the anchor assembly is deployed from the needle to engage a tissue plane (e.g. the prostatic capsule) and provide counter traction to the urethral end thereby locking the compression or displacement of the median lobe.

Figure 11D:
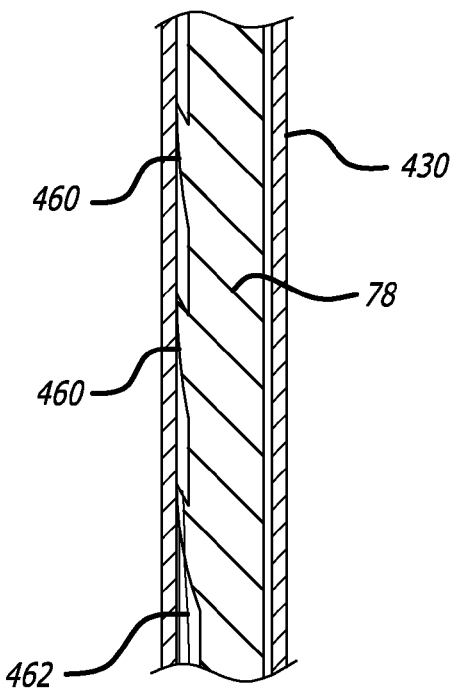
FIG. 11D is a partial cross-sectional view, depicting a means to releasably hold a suture or tension member.

Such a device could be stand-alone, i.e. not requiring a TRUS probe. The device could accommodate insertion of an ultrasound or other imaging probe into the device for guidance and could have an integrated disposable imaging system. A handle on the needle device can be added to fully or partially automate connector delivery. The handle can have user settings for needle depth or implant length. The connector length can be fixed in the manufacturing factory and available in different lengths to the market. The user can then select the appropriate length based on TRUS or other imaging data. Also, the needle or suture can be coated or doped with antimicrobial materials such as silver and the connector length could be set at the time of delivery. It is contemplated that the second end of the connector could be replaced with a series of barbs or hooks which engage in tissue bulk, thereby obviating the need to deploy onto a tissue plane. Such barbs or hooks 460 can be configured to be compressed when held in a needle 430 and to engage a tensioning wire 462 (See FIG. 11D). As the suture 78 is released upward and exits the needle, the barbs 460 can flex open to thereby release the tensioning wire 462 and free the suture 78. Further, barbs could be used to engage on a tissue plane or in tissue bulk and provide a one-size-fits-all feature and the connector could have an elastic component. A Foley catheter or other device could be used to locate the urethra on the TRUS image. In fact, a customized Foley catheter could provide a specific deployment target and a Doppler flow feature on the ultrasound could be used in conjunction with a Foley catheter to further enhance the target.

Figure 12:
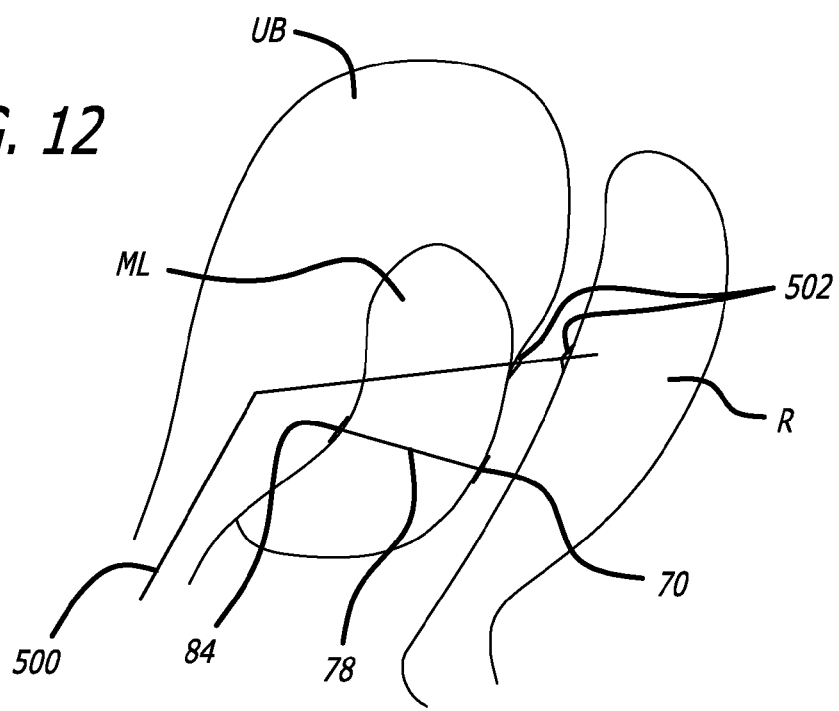
FIG. 12 is a cross-sectional view, depicting a treatment approach involving a blunt dissector.
Figure 13A:
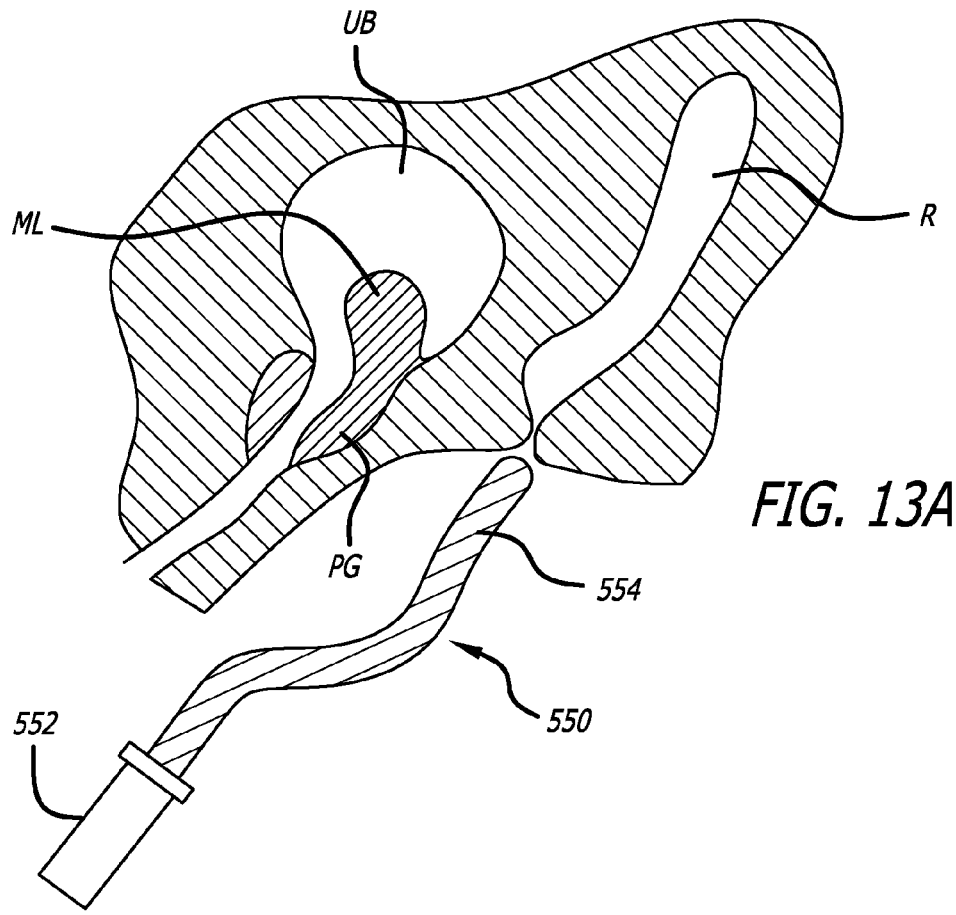
FIGS. 13A-D are cross-sectional views, depicting a treatment approach involving a rectal insertion tool.
Figure 13B:
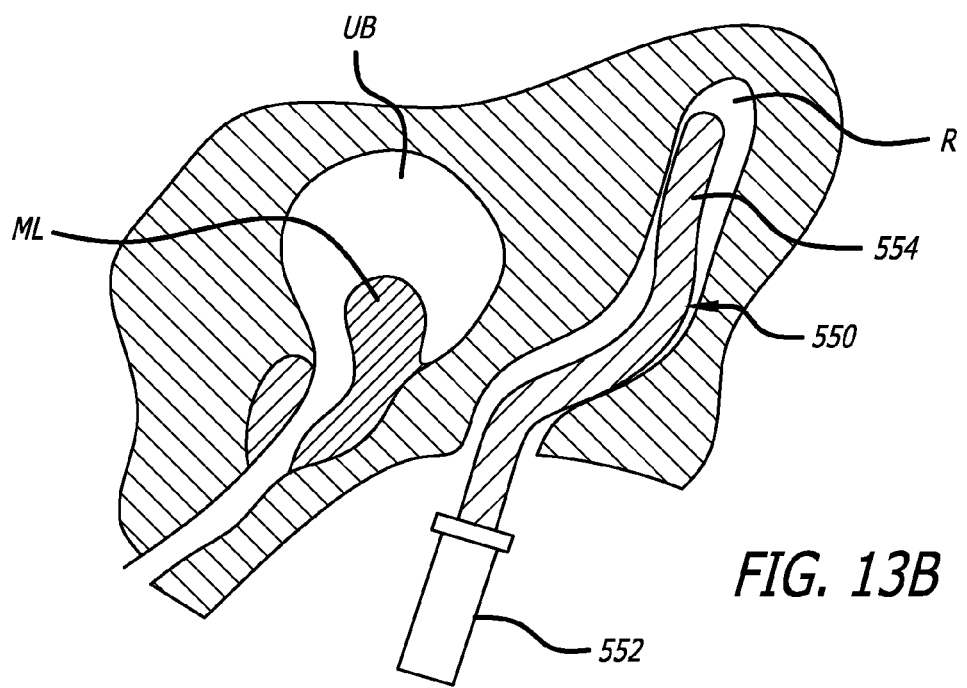
Figure 13C:
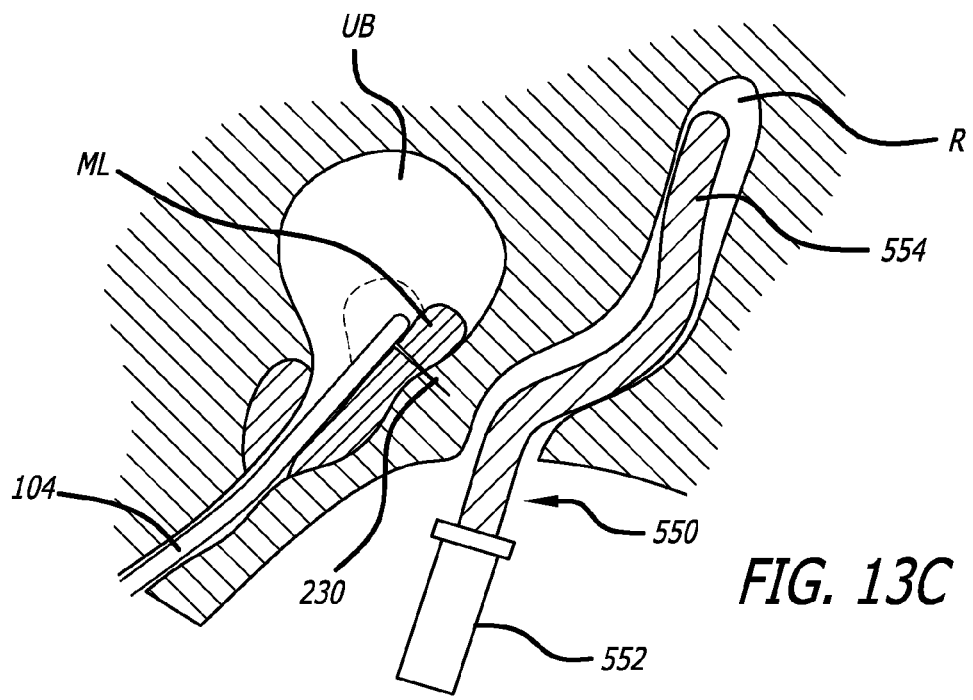
Figure 13D:
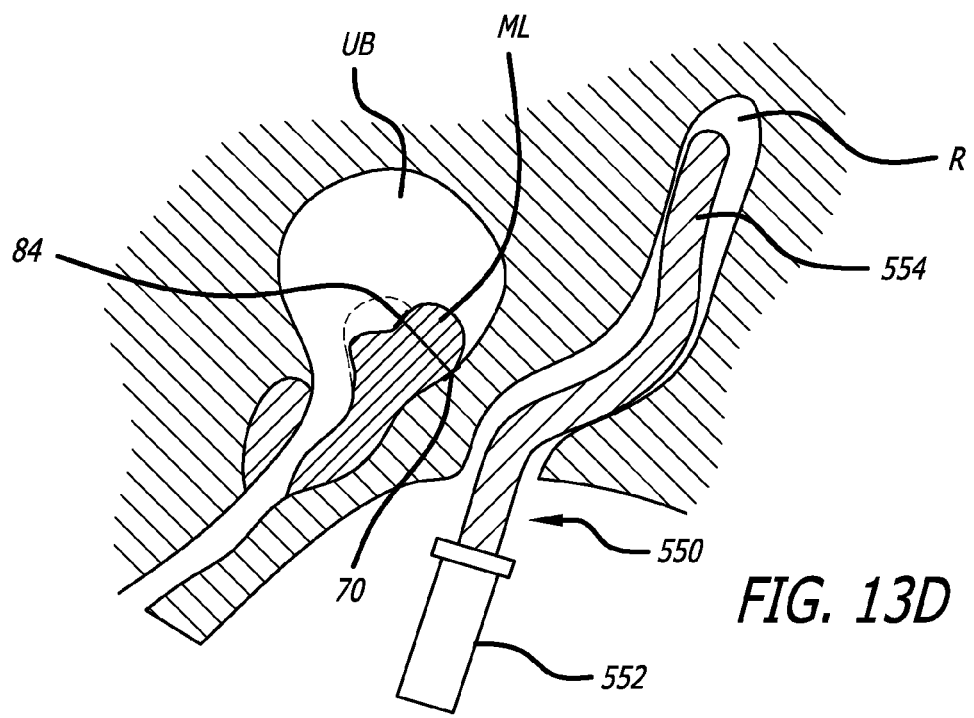

FIG. 12 depicts another approach which addresses potential space limitations between the rectum R and the bladder UB. In such a scenario, a blunt dissector 500 can be employed to create or modify anatomy. The blunt dissector 500 can be an elongate instrument having a length and profile sufficient to extend from outside a patient, through the urethra and to the space between the bladder UB and rectum R. Further, the device 500 can be formable or include an articulating arm to angle the device into position. At a distal end portion of the device can be provided staged barbs 502 intended to engage tissue between the rectum R and bladder UB. The device 500 can further include telescoping tubes or other structure accomplishing the translation of one barb with respect to another so that a desired amount of spacing can be achieved between the bladder and rectum. The dissector 500 can be held in place during a procedure involving implanting an anchor assembly to manipulate the median lobe ML so that puncture of the rectum R is avoided. Furthermore, one or more depth sensors or markers can be incorporated into the dissector 500 to thereby prevent penetration of the rectum.

With reference now to FIGS. 13A-D, yet another approach to avoiding puncture of the rectum R is presented. Here, a rectum manipulator tool 550 is inserted into the rectum R to move the rectum away from the prostate gland PG. The tool 550 includes a handle 552 for grasping by the operator and a curved shaft 554 extending from the handle. The contour of the curved shaft 554 can be selected so that the desired displacement of the rectum R can be achieved by simply inserting the tool within the rectum R. The tool 550 can also be rotated to gain the desired effect. Upon placement of the tool 550 into the rectum R, a larger space between the rectum R and the prostate PG is provided so that an anchor assembly can be deployed at the interventional site by a needle 230 projected from the distal portion 104 of a delivery device. After implantation, the anchor assembly operates to displace the median lobe away from the opening to the bladder UB. The displaced median lobe ML is shown in the figures with cross hatching. Again, depth sensors or indicators can be incorporated into the devices to avoid penetration of the rectum wall.

Figure 14A:
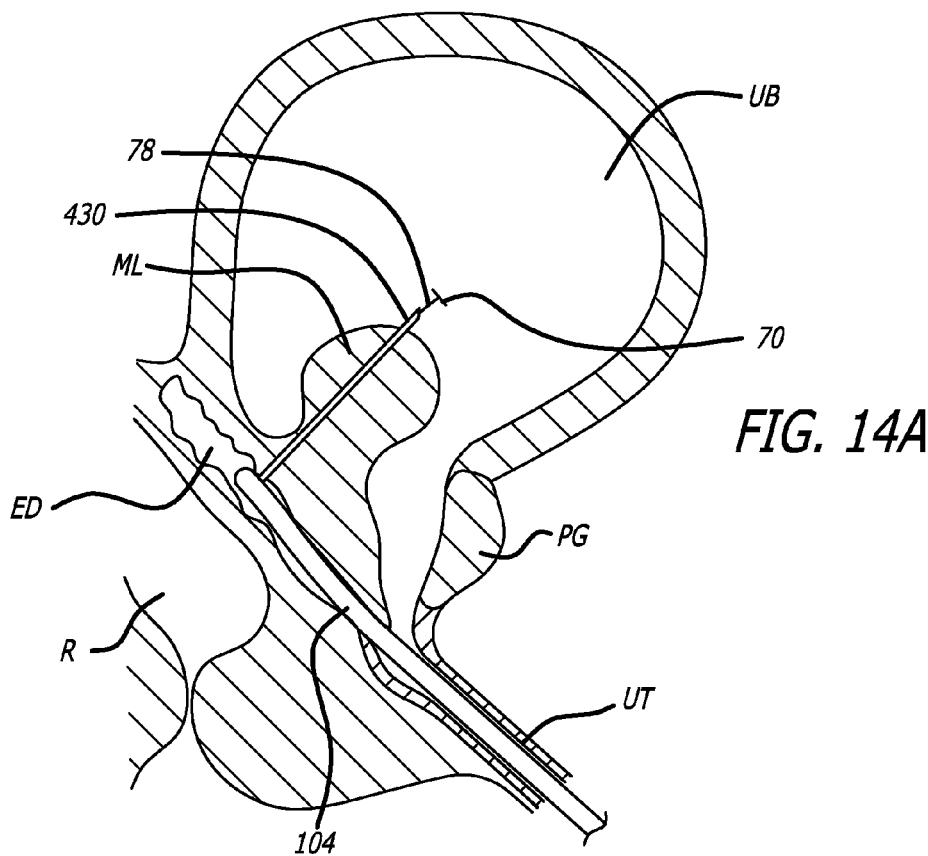
FIGS. 14A-C are cross-sectional views, depicting details of other approaches to displacing a median lobe of a prostate.
Figure 14B:
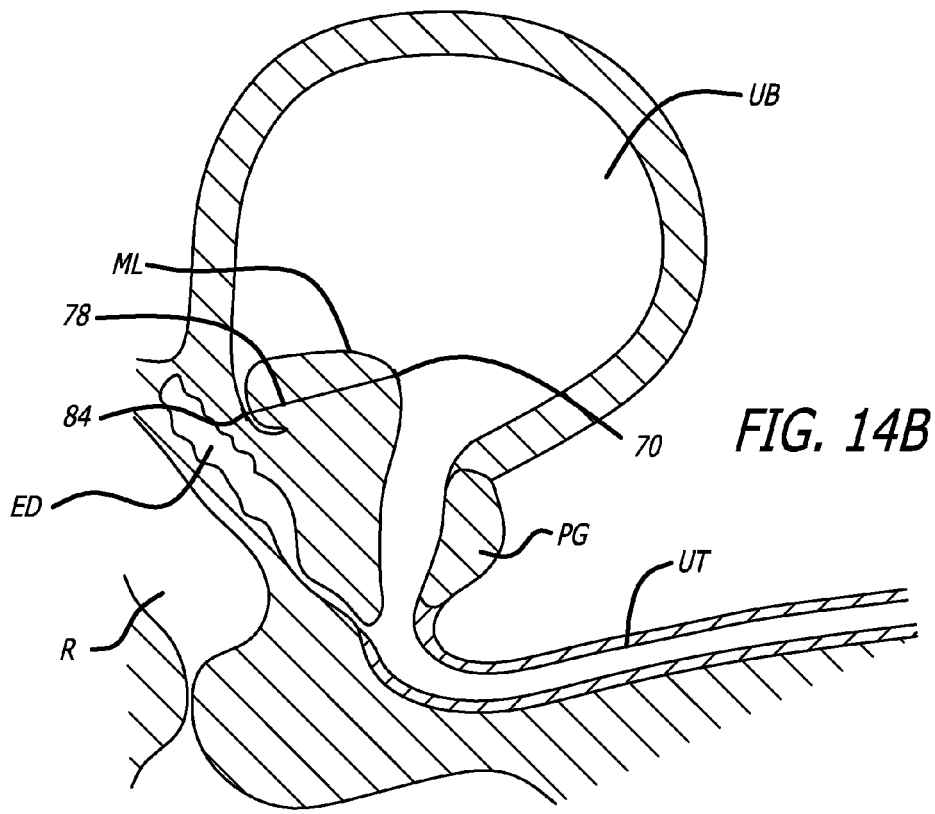

With specific reference now to FIGS. 14A-B, an approach to median lobe ML retraction involving the ejaculatory duct ED is described. Here, the elongate end 104 of the anchor delivery device is inserted into the urethra UT and guided into the ejaculatory duct ED. A needle 430 is advanced through the enlarged median lobe ML and into the urinary bladder UB. The needle 430 is retracted, exposing a distal anchor member 70 attached to a connector 78. The anchor 70 and connector 78 are tensioned, moving the enlarged median lobe ML towards the posterior wall of the prostate gland PG and away from the bladder neck. A proximal anchor 84 is deployed onto the connector 78 on the ejaculatory duct side, and the connector is cut. The tension and position of the anchors retract the enlarged median lobe away from the bladder neck, reducing the obstruction of the bladder neck and urethra UT. Again, here, multiple anchors deployed at various angles and directions can be employed to accomplish the desired retraction.

Figure 14C:
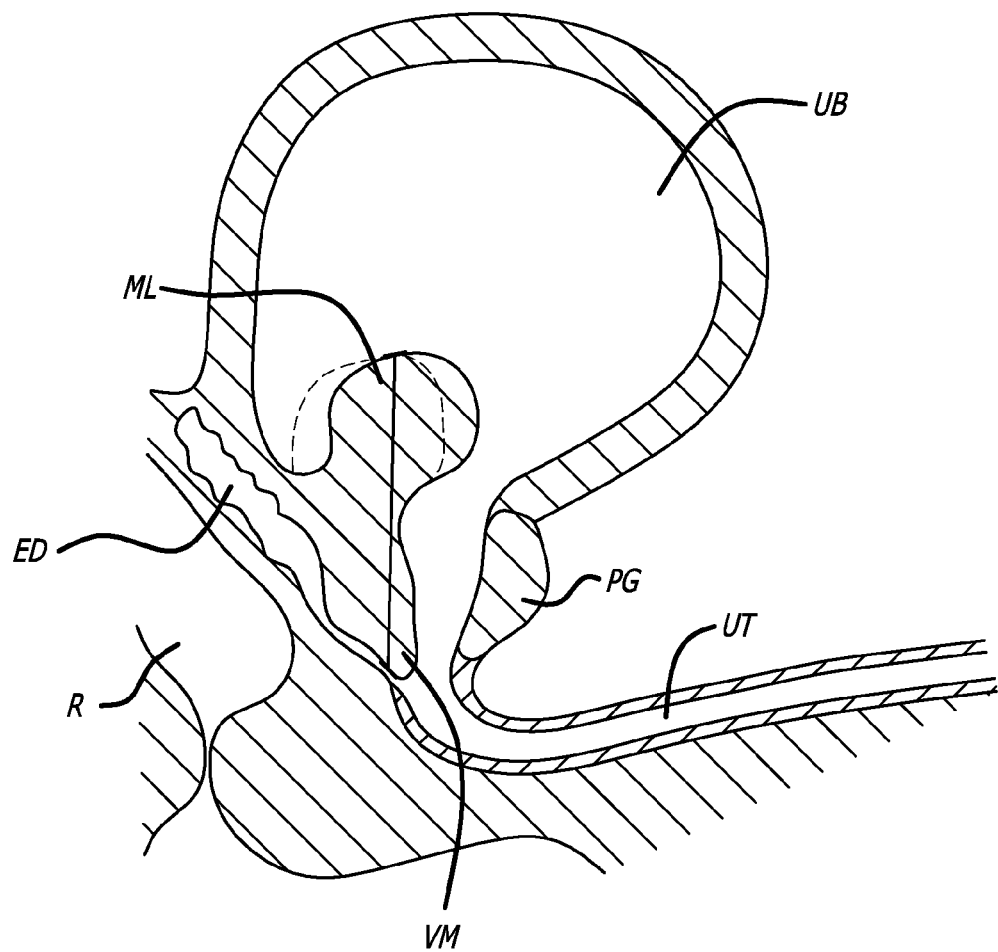

Alternatively, median lobe ML retraction can be accomplished by inserting the needle anatomically distal to or near the verumontanum VM and advanced in a cranial and slightly posterior direction to penetrate through the median lobe ML and exit the median lobe ML near the bladder neck. Once the needle is through the median lobe ML, the first anchor 70 is deployed into the urinary tract or on the surface of the median lobe that is in the bladder space. The needle is then fully or partially withdrawn and tension is applied to the connector 78. The needle is then fully withdrawn and the second anchor 84 is connected to the connector 78 (See FIG. 14C; dotted lines depicting median lobe translation). In an alternative approach, the needle is advanced in a cranial direction to penetrate through the median lobe and the first anchor is deployed on the surface of the median lobe that is in the bladder space or in the urinary tract. The needle is then fully or partially withdrawn and tension is applied to the connector to invert a portion of the median lobe in on itself. The needle is then fully withdrawn and the second anchor is connected to the connector.

During the procedure, a second catheter (not shown) with a vision system may be advanced into the urinary bladder UB to allow verification of anchor placement and tensioning of the enlarged median lobe ML from within the urinary bladder UB. The catheter or device may be flexible, rigid or semi-rigid. The needle may exit at the tip of the device, or may exit at the side of the device. Some portion or the entire catheter or device may have articulation control to allow for navigating and positioning.

Figure 15A:
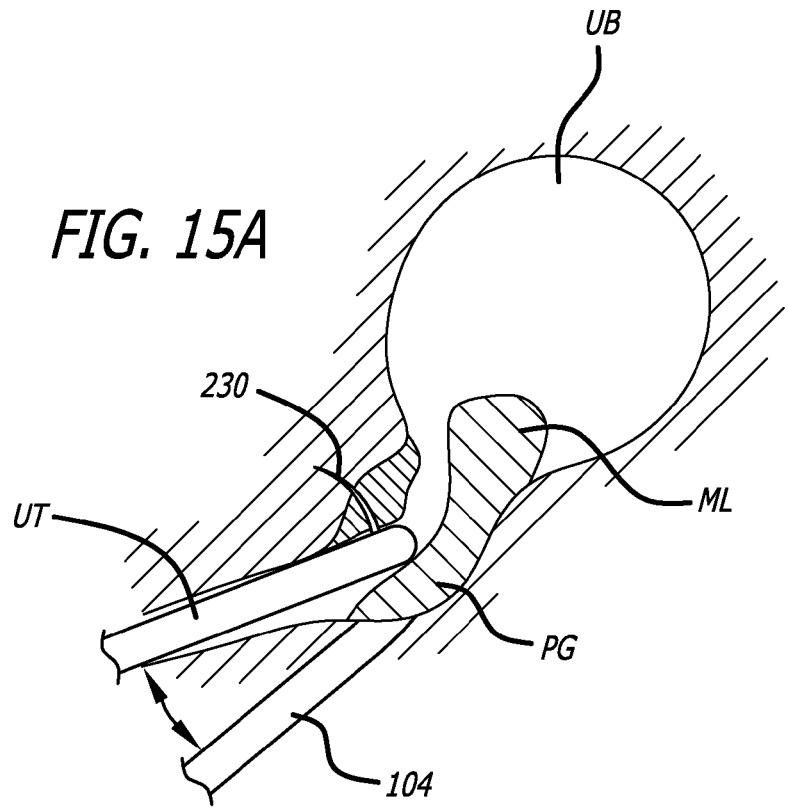
FIGS. 15A-B are cross-sectional views, depicting an alternative treatment approach.
Figure 15B:
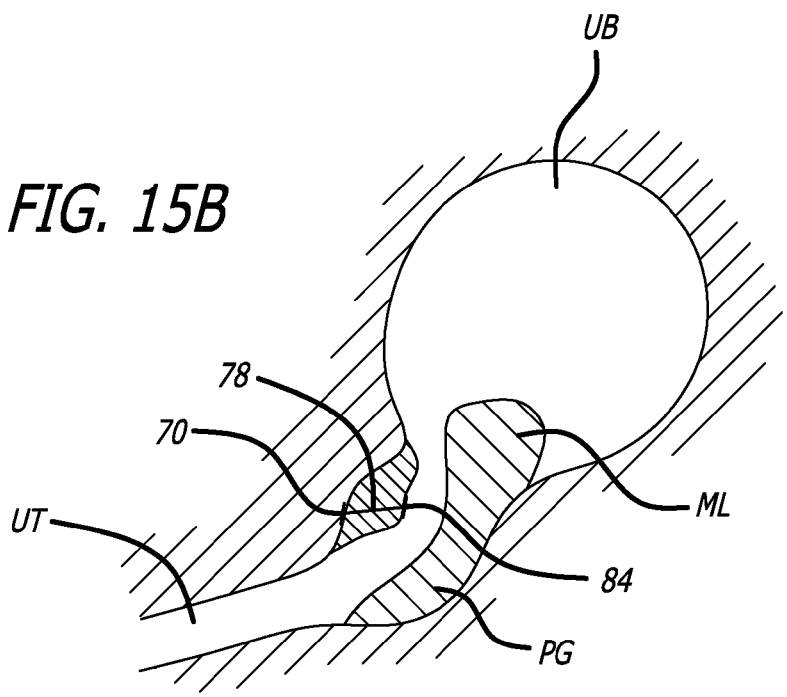

Furthermore, as shown in FIGS. 15A-B, rather than retracting the median lobe MB, an opposite side of the prostatic urethra UT can be retracted away from the median lobe to open the urethra. To accomplish this, the anchor delivery device can again be advanced within the urethra UT and employed to implant an anchor assembly. In particular, one or more anchor assemblies are deployed between the 11 and 10'oclock positions through an anterior wall of the prostate PG in an anatomically distal direction. Prior to deploying the needle 230, the shaft 104 of the delivery device is angled causing the subsequently deployed needle 230 to point anatomically distally. Upon implantation, the anchor assembly left in the anterior wall of the prostatic urethra UT such that the enlarged median lobe ML cannot close off the bladder neck. An extra-urethral approach can also be taken to implant the anchor assembly and create a larger space through the prostate.

Figure 16:
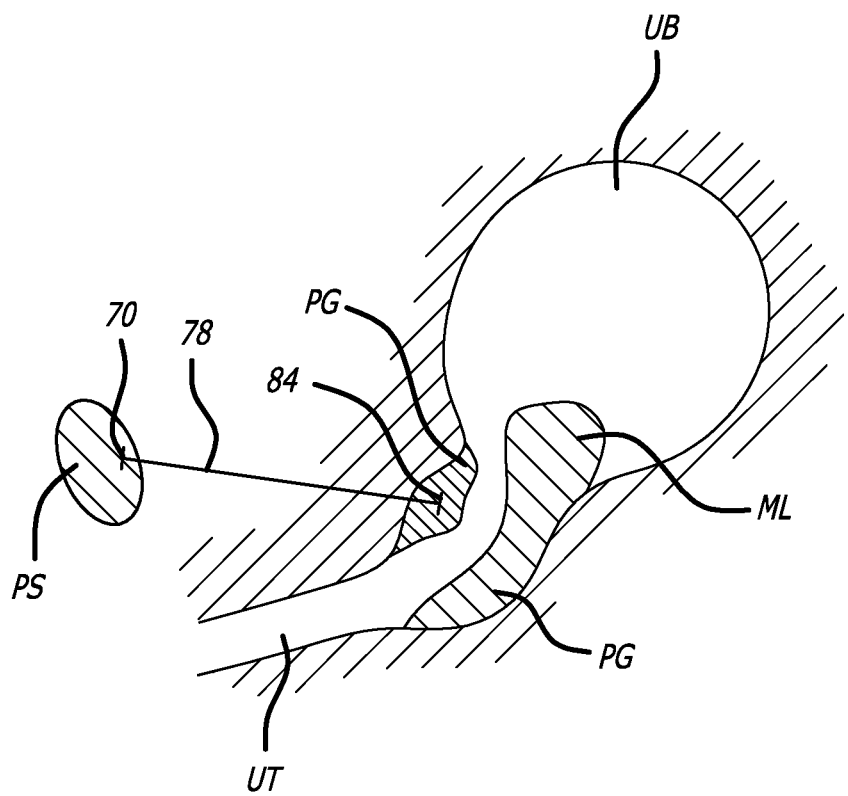
FIG. 16 is a cross-sectional view, depicting yet another alternative treatment approach.

Another related approach to treating a patient suffering from an enlarged median lobe ML is shown in FIG. 16. Here, an anterior portion of the prostate gland PG can be anchored to the pubic symphisis PS using an anchor assembly. In lifting an anterior wall of the prostatic urethra UT, the bladder neck can open in such a way that the intravesicular mass of the median lobe ML is unable to fully close off the bladder neck when the bladder UB is pressurized. Alternatively, rather than anchoring to the pubic symphisis PS, the anterior portion of the prostate PB can be anchored to surrounding or adjacent muscle or tissue.

Figure 17A:
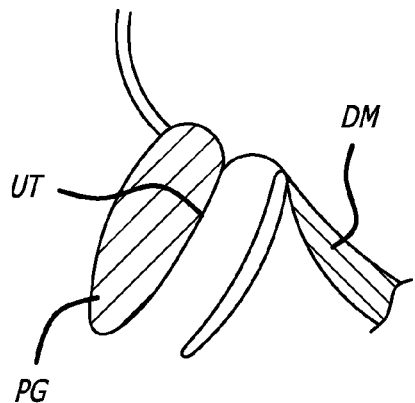
FIGS. 17A-B are cross-sectional views, depicting still yet another alternative treatment approach.
Figure 17B:
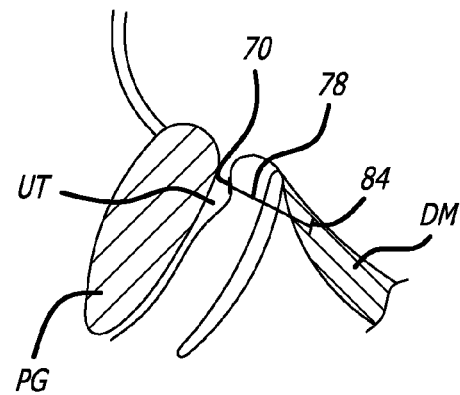

Moreover, other sections of the prostate can similarly be anchored to surrounding tissue (FIGS. 17A-B). That is, a portion of the posterior proximal prostate PG can be anchored to detrusor muscle DM to shift a high bladder neck downwardly. In this way, a path for normal biological functioning is opened through the prostatic urethra UT.

Figure 18A:
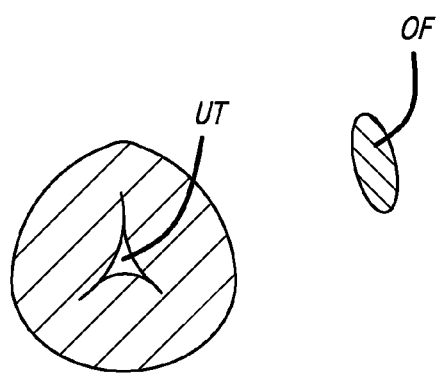
FIGS. 18A-B are cross-sectional views of another treatment approach.
Figure 18B:
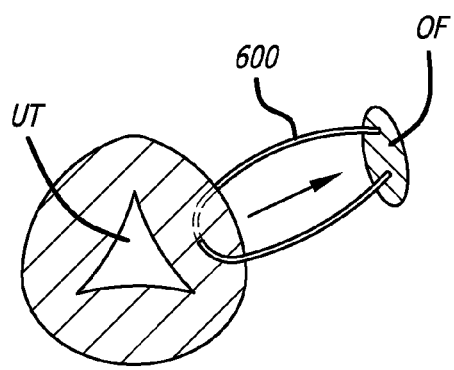

It also may be desirable and less invasive to open the prostatic urethra UT without needing to instrument the urethra UT. One challenge is, however, finding the urethral wall to pull open. In one approach (See FIGS. 18A-B), no reliance is placed upon urethral wall access to open the prostatic urethra. For example, a high surface area object or material can be used to displace the subepithelial (suburethral) tissue away from the lumen of the prostate PG. This can be done with, for instance, a mesh material 600 implanted through the obturator foramen OF and attached thereto.

Accordingly, the present invention contemplates both pushing directly on anchor portions of an anchor assembly as well as pushing directly upon the connector of the anchor assembly. Moreover, as presented above, the distal or first anchor component is advanced and deployed through a needle assembly and at least one component of the proximal or second anchor component is advanced and deployed from a housing portion of the anchor deployment device. Further, either a single anchor assembly or multiple anchor assemblies can be delivered and deployed at an intervention site by the deployment device. Additionally, a single anchor assembly component can for example, be placed on one side of a prostate or urethra while multiple anchor assembly components can be positioned along an opposite or displaced position of such anatomy. The number and locations of the anchor assemblies can thus be equal and/or symmetrical, different in number and asymmetrical, or simply asymmetrically placed. In the context of prostate treatment, the present invention is used for the compression of the prostate gland and the opening of the prostatic urethra, the delivering of an implant at the interventional site, and applying tension between ends of the implant. Moreover, drug delivery is both contemplated and described as a further remedy in BPH and over active bladder treatment as well as treating prostate cancer and prostatitis.

Once implanted, the anchor assembly of the present invention accomplishes desired tissue manipulation, approximation, compression or retraction as well as cooperates with the target anatomy to provide an atraumatic support structure. In one preferred embodiment, the shape and contour of the anchor assembly is configured so that the assembly invaginates within target tissue, such as within natural folds formed in the urethra by the opening of the urethra lumen by the anchor assembly. In fact, in situations where the anchor assembly is properly placed, wispy or pillowy tissue in the area collapses around the anchor structure. Eventually, the natural tissue can grow over the anchor assembly and new cell growth occurs over time. Such cooperation with target tissue facilitates healing and avoids unwanted side effects such as calcification or infection at the interventional site.

Subsequent to the interventional procedure, the patient can be directed to take alpha blockers for 2-4 weeks. Anti-inflammatory medicine can also be taken.

Furthermore, in addition to an intention to cooperate with natural tissue anatomy, the present invention also contemplates approaches to accelerate healing or induce scarring. Manners in which healing can be promoted can include employing abrasive materials, textured connectors, biologics and drugs.

Additionally, it is contemplated that the components of the anchor assembly or selected portions thereof (of any of the anchor assemblies described or contemplated), can be coated or embedded with therapeutic or diagnostic substances (e.g. drugs or therapeutic agents). Again, in the context of treating a prostate gland, the anchor assembly can be coated or imbedded with substances such as 5-alpha-reductase which cause the prostate to decrease in size. Other substances contemplated include but are not limited to phytochemicals generally, alpha-1a-adrenergic receptor blocking agents, smooth muscle relaxants, and agents that inhibit the conversion of testosterone to dihydrotestosterone. In one particular approach, the connector can for example, be coated with a polymer matrix or gel coating which retains the therapeutic or diagnostic substance and facilitates accomplishing the timed release thereof. Additionally, it is contemplated that bacteriostatic coatings as well as analgesics and antibiotics for prostatitis and other chemical coatings for cancer treatment, can be applied to various portions of the anchor assemblies described herein. Such coatings can have various thicknesses or a specific thickness such that it along with the connector itself matches the profile of a cylindrical portion of an anchor member affixed to the connector. Moreover, the co-delivery of a therapeutic or diagnostic gel or other substances through the implant deployment device or another medical device (i.e. catheter), and moreover an anchor assembly including the same, is within the scope of the present invention as is radio-loading devices (such as a capsular or distal ends of implants for cancer or other treatment modalities). In one such approach, the deployment device includes a reservoir holding the gel substance and through which an anchor device can be advance to pick up a desired quantity of therapeutic or diagnostic gel substance.

It is to be recognized that the timing of the dual advancement of the needle and connector assemblies and subsequent relative motion between the assemblies is coordinated. That is, the needle assembly first provides access to an interventional site and then the connector assembly is left extending beyond a terminal end of the needle assembly through the relative motion of the needle and connector assemblies.

It is further contemplated that in certain embodiments, the anchor delivery device can include the ability to detect forces being applied thereby or other environmental conditions. Various sections of the device can include such devices and in one contemplated approach sensors can be placed along the needle assembly. In this way, an operator can detect for example, whether the needle has breached the target anatomical structure at the interventional site and the extent to which such breaching has occurred. Other sensors which can detect particular environmental features can also be employed such as blood or other chemical or constituent sensors. Moreover, one or more pressure sensors or sensors providing feedback on the state of deployment of the anchor assembly during delivery or after implantation are contemplated. For example, tension or depth feedback can be monitored by these sensors. Further, such sensors can be incorporated into the anchor assembly itself, other structure of the deployment device or in the anatomy.

Moreover, it is to be recognized that the foregoing procedure is reversible. In one approach, the connection of an anchor assembly can be severed and a proximal (or second) anchor component removed from the patient's body. For example, the physician can cut the connector and simultaneously remove the second anchor previously implanted for example, in the patient's urethra using electrosurgical, surgical or laser surgical devices used in performing transurethral prostate resection.

An aspect that the various embodiments of the present invention provide is the ability to deliver an anchor assembly having a customizable length, each anchor assembly being implanted at a different location without having to remove the device from the patient. Other aspects of the various embodiments of the present invention are load-based delivery, of an anchor assembly, anchor assembly delivery with a device having integrated connector, (e.g. suture), cutting, and anchor assembly delivery with an endoscope in the device. The delivery device is uniquely configured to hold the suture with tension during delivery to help ensure that the first anchor component sits firmly against a tissue plane (e.g., the outer capsule of the prostate) and is held relatively firm as the second anchor component is attached to the connector and the delivery device. In this aspect, the needle assembly acting as a penetrating member is cooperatively connected to a mechanism which pulls on the anchor while the needle assembly is retracted.

It is to be recognized that various materials are within the scope of the present invention for manufacturing the disclosed devices. Moreover, one or more components such as distal anchor, proximal anchor, and connector, of the one or more anchor devices disclosed herein can be completely or partially biodegradable or biofragmentable.

Further, as stated, the devices and methods disclosed herein can be used to treat a variety of pathologies in a variety of lumens or organs comprising a cavity or a wall. Examples of such lumens or organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Finally, it is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

Thus, it will be apparent from the foregoing that, while particular forms of the invention have been illustrated and described, various modifications can be made without parting from the spirit and scope of the invention.

We claim:

1. A method for treating benign prostatic hypertrophy having an enlarged median lobe, comprising:
    implanting a first anchor on a first side of the median lobe; and
    implanting a second anchor on a second side of the median lobe with a connector between the first and second anchors to retract the median lobe away from an urethra opening to increase luminal area.

2. The method of claim 1, further comprising inserting an anchor delivery device within the urethra; actuating the anchor delivery device.

3. The method of claim 2, further comprising incorporating a depth sensor or indicator into the anchor delivery device so that penetration of a rectum is avoided.

4. The method of claim 1, further comprising removing the anchor delivery device from the urethra.

5. The method of claim 1, further comprising compressing the median lobe with the anchor delivery device.

6. The method of claim 1, further comprising advancing the anchor delivery device into an ejaculatory duct.

7. The method of claim 1, further comprising forming a channel in the median lobe with an anchor delivery device.

8. The method of claim 7, further comprising rotating the anchor delivery device and actuating the anchor delivery device to eject a needle assembly through the median lobe.

9. The method of claim 8, further comprising manipulating the anchor delivery device to implant the first anchor.

10. The method of claim 9, further comprising causing the anchor delivery device to implant the second anchor.

11. The method of claim 10, further comprising again rotating the anchor delivery device and deploying a second anchor assembly across the median lobe.

12. The method of claim 11, further comprising further rotation of the anchor delivery device and implanting one or more subsequent anchor assemblies across the median lobe.

13. The method of claim 12, further comprising creating one or more permanent valleys through the median lobe.

14. The method of claim 1, further comprising advancing a needle assembly through the ejaculatory duct and the median lobe.

15. The method of claim 14, further comprising implanting the first anchor within the urinary bladder and in apposition with the median lobe.

16. The method of claim 15, further comprising implanting the second anchor within the ejaculatory duct.

17. The method of claim 16, further comprising rotating the anchor delivery device.

18. The method of claim 17, further comprising implanting a second anchor assembly from the ejaculatory duct and across the median lobe.

19. The method of claim 1, further comprising anchoring the median lobe to the pubic symphysis.

20. The method of claim 1, further comprising anchoring the median lobe to the detrusor muscle.

21. A method for treating benign prostatic hypertrophy, comprising:
    assessing an anatomy of a median lobe;
    actuating an anchor delivery device to implant a first anchor on a first side of the median lobe and a second anchor on a second side of the median lobe to thereby retract the medial lobe to increase luminal flow through an urethra; and
    removing the anchor delivery device from the urethra.

22. The method of claim 21, further comprising taking an extra-urethral approach to implant an anchor assembly across the median lobe.

23. A method for treating benign prostatic hypertrophy, comprising:
    assessing an anatomy of a median lobe;
    activating an anchor delivery device to implant first and second anchors on a first side of a median lobe and a third anchor on a second side of a median lobe to increase luminal flow through a urethra, wherein the first and second anchors are placed to create a 6 o'clock net force displacement of the median lobe; and
    removing the anchor delivery device from the urethra.

24. The method of claim 23, further comprising implanting a fourth anchor on the second side of the median lobe.

* * * * *